United States Patent
Shimoni et al.

(10) Patent No.: US 10,227,559 B2
(45) Date of Patent: Mar. 12, 2019

(54) COMPOUNDED MEDIA POWDER FORMULATION AND METHOD OF PREPARATION OF LIQUID MEDIUM FOR CELL CULTURE

(71) Applicant: Bayer HealthCare LLC, Whippany, NJ (US)

(72) Inventors: Yuval Shimoni, Berkeley, CA (US); Volker Möhrle, Köln (DE)

(73) Assignee: Bayer HealthCare LLC, Whippany, NJ (US)

( * ) Notice: Subject to any disclaimer, the term of this patent is extended or adjusted under 35 U.S.C. 154(b) by 227 days.

(21) Appl. No.: 15/302,488

(22) PCT Filed: Apr. 7, 2015

(86) PCT No.: PCT/US2015/024780
§ 371 (c)(1),
(2) Date: Oct. 7, 2016

(87) PCT Pub. No.: WO2015/157335
PCT Pub. Date: Oct. 15, 2015

(65) Prior Publication Data
US 2017/0191025 A1    Jul. 6, 2017

Related U.S. Application Data

(60) Provisional application No. 61/978,027, filed on Apr. 10, 2014.

(51) Int. Cl.
| | |
|---|---|
| *C12N 5/07* | (2010.01) |
| *C12N 5/02* | (2006.01) |
| *C12N 5/00* | (2006.01) |

(52) U.S. Cl.
CPC ......... *C12N 5/0037* (2013.01); *C12N 5/0018* (2013.01); *C12N 5/0031* (2013.01);
(Continued)

(58) Field of Classification Search
None
See application file for complete search history.

(56) References Cited

U.S. PATENT DOCUMENTS

| | | | |
|---|---|---|---|
| 4,584,100 A | 4/1986 | Choquenet et al. | |
| 4,766,075 A | 8/1988 | Goeddel et al. | |

(Continued)

FOREIGN PATENT DOCUMENTS

| | | | | |
|---|---|---|---|---|
| WO | WO-0236735 A2 | * | 5/2002 | ............... C12N 1/00 |
| WO | 2007047504 A2 | | 4/2007 | |
| WO | WO-2013096858 A1 | * | 6/2013 | ........... C12N 5/0018 |

OTHER PUBLICATIONS

Baumann; et al., "Dexamethasone regulates the program of secretory glycoprotein synthesis in hepatoma tissue culture cells", Apr. 1, 1980, vol. 85, 1-8.

(Continued)

*Primary Examiner* — Louise Humphrey
*Assistant Examiner* — Charles Zoltan Constantine
(74) *Attorney, Agent, or Firm* — Timothy H. Joyce

(57) ABSTRACT

The present invention provides a compounded cell culture medium powder formulation comprising: a basal medium powder and a cell culture media supplement, wherein the cell culture media supplement comprises and one or more salts; one or more growth factors; one or more inorganic ions; an amino acid supplement comprising one or more of asparagine, glutamine, histidine, and serine; one or more buffers; and one or more anti-foaming agents. The invention further provides methods of making a compounded cell culture medium powder formulation methods of making a cell culture medium for growing mammalian cells and (Continued)

methods of producing a protein of interest by culturing cells in the cell culture medium and isolating the protein of interest.

1 Claim, 3 Drawing Sheets

Specification includes a Sequence Listing.

(52) U.S. Cl.
CPC ...... *C12N 2500/05* (2013.01); *C12N 2500/14* (2013.01); *C12N 2500/22* (2013.01); *C12N 2500/24* (2013.01); *C12N 2500/32* (2013.01); *C12N 2500/34* (2013.01); *C12N 2500/42* (2013.01); *C12N 2500/44* (2013.01); *C12N 2500/46* (2013.01); *C12N 2500/60* (2013.01); *C12N 2501/10* (2013.01)

(56) References Cited

U.S. PATENT DOCUMENTS

| | | | |
|---|---|---|---|
| 4,853,330 | A | 8/1989 | Goeddel et al. |
| 5,185,259 | A | 2/1993 | Goeddel et al. |
| 5,330,971 | A | 7/1994 | Wells et al. |
| 6,232,117 | B1 | 5/2001 | Mather |
| 6,383,810 | B2 | 5/2002 | Fike et al. |
| 6,900,056 | B2 | 5/2005 | Lee et al. |
| 7,632,921 | B2 | 12/2009 | Pan et al. |
| 8,129,504 | B2 | 3/2012 | Prior et al. |
| 9,012,180 | B2 | 4/2015 | Drapeau et al. |
| 9,284,371 | B2 | 3/2016 | Pla et al. |
| 2006/0003447 | A1 | 1/2006 | Fike et al. |
| 2011/0262965 | A1 | 10/2011 | Barrett et al. |

OTHER PUBLICATIONS

Bovenschen; et al., "Low Density Lipoprotein Receptor-related Protein and Factor IXa Share Structural Requirements for Binding to the A3 Domain of Coagulation Factor VIII", Mar. 14, 2003, vol. 278 Issue No. 11, 9370-9377.

Butler; M., "A Comparative Review of Microcarriers Available for the Growth of Anchorage-dependent Animal Cells", 1988, vol. 3, 283-303, Chapter 12, Animal Cell Biotechnology vol. 3, Academic Press, Michigan, Editors Spier, R, and Griffiths, J.

Graham; et al., "Characteristics of a Human Cell Line Transformed by DNA from Human Adenovirus Type 5", Jan. 7, 1977, vol. 36 Issue No. 59, 59-72, Journal of General Virology.

"International Search Report & Written Opinion of International Application No. PCT/US2015/024780 dated Jul. 16, 2015".

Lubiniecki; et al., "Selected Strategies for Manufacture and Control of Recombinant Tissue Plasminogen Activator Prepared from Cell Cultures", Spier et al., eds., 1989, 442-451, Advances in animal cell biology and technology for bioprocesses. Butterworths, London.

Luckow; et al., "Trends in the Development of Baculovirus Expression Vectors", Jan. 1988, vol. 6, 47-55, Nature Biotechnology.

Mather; Jennie P., "Establishment and Characterization of Two Distinct Mouse Testicular Epithelial Cell Lines", Aug. 1, 1980, vol. 23 Issue No. 1, 243-252, Biology of Reproduction.

Routledge; Sarah J., "Beyond De-Foaming: The Effects of Antifoams on Bioprocess Productivity", Oct. 2012, vol. 3 Issue No. 4, 1-7, Computational and Structural Biotechnology Journal.

Simonsen; et al., "Isolation and expression of an altered mouse dihydrofolate reductase cDNA", May 1, 1983, vol. 80 Issue No. 9, 2495-2499, Proceedings of the National Academy of Sciences.

Urlaub; et al., "Isolation of Chinese Hamster Cell Mutants Deficient in Dihydrofolate Reductase Activity", Jul. 1980, vol. 77 No. 7, 4216-4220, Proceedings of the National Academy of Sciences.

* cited by examiner

Compounded Media

- One base media powder containing all components (same: sources, composition & final concentrations)
- Compounded media is prepared in an animal-component free facility and is chemically defined Compounded Base Media → media tank ← EDTA/Ferrous Sulfate Solution

SEQUENCE LISTING

<160> NUMBER OF SEQ ID NOS: 6

<210> SEQ ID NO 1
<211> LENGTH: 2351
<212> TYPE: PRT
<213> ORGANISM: Homo sapiens

<400> SEQUENCE: 1

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

-continued

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

```
Phe Asp Ser Leu Gln Leu Ser Val Cys Leu His Glu Val Ala Tyr Trp
            645                 650                 655
Tyr Ile Leu Ser Ile Gly Ala Gln Thr Asp Phe Leu Ser Val Phe Phe
        660                 665                 670
Ser Gly Tyr Thr Phe Lys His Lys Met Val Tyr Glu Asp Thr Leu Thr
            675                 680                 685
Leu Phe Pro Phe Ser Gly Glu Thr Val Phe Met Ser Met Glu Asn Pro
690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
            755                 760                 765
Ser Thr Arg Gln Lys Gln Phe Asn Ala Thr Thr Ile Pro Glu Asn Asp
770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
                820                 825                 830
Glu Thr Phe Ser Asp Asp Pro Ser Pro Gly Ala Ile Asp Ser Asn Asn
            835                 840                 845
Ser Leu Ser Glu Met Thr His Phe Arg Pro Gln Leu His His Ser Gly
850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
                900                 905                 910
Leu Ala Ala Gly Thr Asp Asn Thr Ser Ser Leu Gly Pro Pro Ser Met
            915                 920                 925
Pro Val His Tyr Asp Ser Gln Leu Asp Thr Thr Leu Phe Gly Lys Lys
            930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Ser Thr Glu Ser Gly Arg Leu Phe
            980                 985                 990
Lys Gly Lys Arg Ala His Gly Pro Ala Leu Leu Thr Lys Asp Asn Ala
            995                 1000                1005
Leu Phe Lys Val Ser Ile Ser Leu Leu Lys Thr Asn Lys Thr Ser
    1010                1015                1020
Asn Asn Ser Ala Thr Asn Arg Lys Thr His Ile Asp Gly Pro Ser
    1025                1030                1035
Leu Leu Ile Glu Asn Ser Pro Ser Val Trp Gln Asn Ile Leu Glu
    1040                1045                1050
Ser Asp Thr Glu Phe Lys Lys Val Thr Pro Leu Ile His Asp Arg
```

-continued

|      |      |      |      |      |      |      |      |      |      |      |
|------|------|------|------|------|------|------|------|------|------|------|
|      | 1055 |      |      | 1060 |      |      | 1065 |      |      |      |

Met Leu Met Asp Lys Asn Ala Thr Ala Leu Arg Leu Asn His Met
        1070            1075            1080

Ser Asn Lys Thr Thr Ser Ser Lys Asn Met Glu Met Val Gln Gln
        1085            1090            1095

Lys Lys Glu Gly Pro Ile Pro Pro Asp Ala Gln Asn Pro Asp Met
        1100            1105            1110

Ser Phe Phe Lys Met Leu Phe Leu Pro Glu Ser Ala Arg Trp Ile
        1115            1120            1125

Gln Arg Thr His Gly Lys Asn Ser Leu Asn Ser Gly Gln Gly Pro
        1130            1135            1140

Ser Pro Lys Gln Leu Val Ser Leu Gly Pro Glu Lys Ser Val Glu
        1145            1150            1155

Gly Gln Asn Phe Leu Ser Glu Lys Asn Lys Val Val Val Gly Lys
        1160            1165            1170

Gly Glu Phe Thr Lys Asp Val Gly Leu Lys Glu Met Val Phe Pro
        1175            1180            1185

Ser Ser Arg Asn Leu Phe Leu Thr Asn Leu Asp Asn Leu His Glu
        1190            1195            1200

Asn Asn Thr His Asn Gln Glu Lys Lys Ile Gln Glu Glu Ile Glu
        1205            1210            1215

Lys Lys Glu Thr Leu Ile Gln Glu Asn Val Val Leu Pro Gln Ile
        1220            1225            1230

His Thr Val Thr Gly Thr Lys Asn Phe Met Lys Asn Leu Phe Leu
        1235            1240            1245

Leu Ser Thr Arg Gln Asn Val Glu Gly Ser Tyr Glu Gly Ala Tyr
        1250            1255            1260

Ala Pro Val Leu Gln Asp Phe Arg Ser Leu Asn Asp Ser Thr Asn
        1265            1270            1275

Arg Thr Lys Lys His Thr Ala His Phe Ser Lys Lys Gly Glu Glu
        1280            1285            1290

Glu Asn Leu Glu Gly Leu Gly Asn Gln Thr Lys Gln Ile Val Glu
        1295            1300            1305

Lys Tyr Ala Cys Thr Thr Arg Ile Ser Pro Asn Thr Ser Gln Gln
        1310            1315            1320

Asn Phe Val Thr Gln Arg Ser Lys Arg Ala Leu Lys Gln Phe Arg
        1325            1330            1335

Leu Pro Leu Glu Glu Thr Glu Leu Glu Lys Arg Ile Ile Val Asp
        1340            1345            1350

Asp Thr Ser Thr Gln Trp Ser Lys Asn Met Lys His Leu Thr Pro
        1355            1360            1365

Ser Thr Leu Thr Gln Ile Asp Tyr Asn Glu Lys Glu Lys Gly Ala
        1370            1375            1380

Ile Thr Gln Ser Pro Leu Ser Asp Cys Leu Thr Arg Ser His Ser
        1385            1390            1395

Ile Pro Gln Ala Asn Arg Ser Pro Leu Pro Ile Ala Lys Val Ser
        1400            1405            1410

Ser Phe Pro Ser Ile Arg Pro Ile Tyr Leu Thr Arg Val Leu Phe
        1415            1420            1425

Gln Asp Asn Ser Ser His Leu Pro Ala Ala Ser Tyr Arg Lys Lys
        1430            1435            1440

Asp Ser Gly Val Gln Glu Ser Ser His Phe Leu Gln Gly Ala Lys
        1445            1450            1455

```
Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Asp Thr Ile Leu Ser Leu Asn Ala Cys
1610                1615                1620

Glu Ser Asn His Ala Ile Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845
```

```
Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
2180                2185                2190

Ser Met Pro Leu Gly Met Glu Ser Lys Ala Ile Ser Asp Ala Gln
2195                2200                2205

Ile Thr Ala Ser Ser Tyr Phe Thr Asn Met Phe Ala Thr Trp Ser
2210                2215                2220

Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
```

```
                2240                2245                2250
Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Val His Leu Phe Asn Ile Ala Lys Pro
        50                  55                  60

Arg Pro Pro Trp Met Gly Leu Leu Gly Pro Thr Ile Gln Ala Glu Val
    65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
        130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255
```

```
Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
```

```
                675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Ser Lys Asn Asn Ala
            725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
            755                 760                 765
Thr Asp Pro Trp Phe Ala His Arg Thr Pro Met Pro Lys Ile Gln Asn
            770                 775                 780
Val Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
                835                 840                 845
Phe Thr Pro Glu Ser Gly Leu Gln Leu Arg Leu Asn Glu Lys Leu Gly
            850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
                900                 905                 910
Tyr Asp Ser Gln Leu Asp Thr Thr Leu Phe Gly Lys Lys Ser Ser Pro
            915                 920                 925
Leu Thr Glu Ser Gly Gly Pro Leu Ser Leu Ser Glu Glu Asn Asn Asp
            930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr Asn Lys Thr Ser Asn Asn Ser Ala
            995                 1000                 1005
Thr Asn Arg Lys Thr His Ile Asp Gly Pro Ser Leu Leu Ile Glu
        1010                 1015                 1020
Asn Ser Pro Ser Val Trp Gln Asn Ile Leu Glu Ser Asp Thr Glu
        1025                 1030                 1035
Phe Lys Lys Val Thr Pro Leu Ile His Asp Arg Met Leu Met Asp
        1040                 1045                 1050
Lys Asn Ala Thr Ala Leu Arg Leu Asn His Met Ser Asn Lys Thr
        1055                 1060                 1065
Thr Ser Ser Lys Asn Met Glu Met Val Gln Gln Lys Lys Glu Gly
        1070                 1075                 1080
Pro Ile Pro Pro Asp Ala Gln Asn Pro Asp Met Ser Phe Phe Lys
        1085                 1090                 1095
```

```
Met Leu Phe Leu Pro Glu Ser Ala Arg Trp Ile Gln Arg Thr His
            1100            1105                1110

Gly Lys Asn Ser Leu Asn Ser Gly Gln Gly Pro Ser Pro Lys Gln
        1115            1120                1125

Leu Val Ser Leu Gly Pro Glu Lys Ser Val Glu Gly Gln Asn Phe
    1130            1135                1140

Leu Ser Glu Lys Asn Lys Val Val Val Gly Lys Gly Glu Phe Thr
    1145            1150                1155

Lys Asp Val Gly Leu Lys Glu Met Val Phe Pro Ser Ser Arg Asn
    1160            1165                1170

Leu Phe Leu Thr Asn Leu Asp Asn Leu His Glu Asn Asn Thr His
    1175            1180                1185

Asn Gln Glu Lys Lys Ile Gln Glu Glu Ile Glu Lys Lys Glu Thr
    1190            1195                1200

Leu Ile Gln Glu Asn Val Val Leu Pro Gln Ile His Thr Val Thr
    1205            1210                1215

Gly Thr Lys Asn Phe Met Lys Asn Leu Phe Leu Leu Ser Thr Arg
    1220            1225                1230

Gln Asn Val Glu Gly Ser Tyr Glu Gly Ala Tyr Ala Pro Val Leu
    1235            1240                1245

Gln Asp Phe Arg Ser Leu Asn Asp Ser Thr Asn Arg Thr Lys Lys
    1250            1255                1260

His Thr Ala His Phe Ser Lys Lys Gly Glu Glu Glu Asn Leu Glu
    1265            1270                1275

Gly Leu Gly Asn Gln Thr Lys Gln Ile Val Glu Lys Tyr Ala Cys
    1280            1285                1290

Thr Thr Arg Ile Ser Pro Asn Thr Ser Gln Gln Asn Phe Val Thr
    1295            1300                1305

Gln Arg Ser Lys Arg Ala Leu Lys Gln Phe Arg Leu Pro Leu Glu
    1310            1315                1320

Glu Thr Glu Leu Glu Lys Arg Ile Ile Val Asp Asp Thr Ser Thr
    1325            1330                1335

Gln Trp Ser Lys Asn Met Lys His Leu Thr Pro Ser Thr Leu Thr
    1340            1345                1350

Gln Ile Asp Tyr Asn Glu Lys Glu Lys Gly Ala Ile Thr Gln Ser
    1355            1360                1365

Pro Leu Ser Asp Cys Leu Thr Arg Ser His Ser Ile Pro Gln Ala
    1370            1375                1380

Asn Arg Ser Pro Leu Pro Ile Ala Lys Val Ser Ser Phe Pro Ser
    1385            1390                1395

Ile Arg Pro Ile Tyr Leu Thr Arg Val Leu Phe Gln Asp Asn Ser
    1400            1405                1410

Ser His Leu Pro Ala Ala Ser Tyr Arg Lys Lys Asp Ser Gly Val
    1415            1420                1425

Gln Glu Ser Ser His Phe Leu Gln Gly Ala Lys Lys Asn Asn Leu
    1430            1435                1440

Ser Leu Ala Ile Leu Thr Leu Glu Met Thr Gly Asp Gln Arg Glu
    1445            1450                1455

Val Gly Ser Leu Gly Thr Ser Ala Thr Asn Ser Val Thr Tyr Lys
    1460            1465                1470

Lys Val Glu Asn Thr Val Leu Pro Lys Pro Asp Leu Pro Lys Thr
    1475            1480                1485
```

-continued

```
Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
```

-continued

```
            1880              1885              1890
Asn Met Glu Arg Asn Cys Arg Ala Pro Cys Asn Ile Gln Met Glu
    1895              1900              1905
Asp Pro Thr Phe Lys Glu Asn Tyr Arg Phe His Ala Ile Asn Gly
    1910              1915              1920
Tyr Ile Met Asp Thr Leu Pro Gly Leu Val Met Ala Gln Asp Gln
    1925              1930              1935
Arg Ile Arg Trp Tyr Leu Leu Ser Met Gly Ser Asn Glu Asn Ile
    1940              1945              1950
His Ser Ile His Phe Ser Gly His Val Phe Thr Val Arg Lys Lys
    1955              1960              1965
Glu Glu Tyr Lys Met Ala Leu Tyr Asn Leu Tyr Pro Gly Val Phe
    1970              1975              1980
Glu Thr Val Glu Met Leu Pro Ser Lys Ala Gly Ile Trp Arg Val
    1985              1990              1995
Glu Cys Leu Ile Gly Glu His Leu His Ala Gly Met Ser Thr Leu
    2000              2005              2010
Phe Leu Val Tyr Ser Asn Lys Cys Gln Thr Pro Leu Gly Met Ala
    2015              2020              2025
Ser Gly His Ile Arg Asp Phe Gln Ile Thr Ala Ser Gly Gln Tyr
    2030              2035              2040
Gly Gln Trp Ala Pro Lys Leu Ala Arg Leu His Tyr Ser Gly Ser
    2045              2050              2055
Ile Asn Ala Trp Ser Thr Lys Glu Pro Phe Ser Trp Ile Lys Val
    2060              2065              2070
Asp Leu Leu Ala Pro Met Ile Ile His Gly Ile Lys Thr Gln Gly
    2075              2080              2085
Ala Arg Gln Lys Phe Ser Ser Leu Tyr Ile Ser Gln Phe Ile Ile
    2090              2095              2100
Met Tyr Ser Leu Asp Gly Lys Lys Trp Gln Thr Tyr Arg Gly Asn
    2105              2110              2115
Ser Thr Gly Thr Leu Met Val Phe Phe Gly Asn Val Asp Ser Ser
    2120              2125              2130
Gly Ile Lys His Asn Ile Phe Asn Pro Pro Ile Ile Ala Arg Tyr
    2135              2140              2145
Ile Arg Leu His Pro Thr His Tyr Ser Ile Arg Ser Thr Leu Arg
    2150              2155              2160
Met Glu Leu Met Gly Cys Asp Leu Asn Ser Cys Ser Met Pro Leu
    2165              2170              2175
Gly Met Glu Ser Lys Ala Ile Ser Asp Ala Gln Ile Thr Ala Ser
    2180              2185              2190
Ser Tyr Phe Thr Asn Met Phe Ala Thr Trp Ser Pro Ser Lys Ala
    2195              2200              2205
Arg Leu His Leu Gln Gly Arg Ser Asn Ala Trp Arg Pro Gln Val
    2210              2215              2220
Asn Asn Pro Lys Glu Trp Leu Gln Val Asp Phe Gln Lys Thr Met
    2225              2230              2235
Lys Val Thr Gly Val Thr Thr Gln Gly Val Lys Ser Leu Leu Thr
    2240              2245              2250
Ser Met Tyr Val Lys Glu Phe Leu Ile Ser Ser Ser Gln Asp Gly
    2255              2260              2265
His Gln Trp Thr Leu Phe Phe Gln Asn Gly Lys Val Lys Val Phe
    2270              2275              2280
```

```
Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 3
<211> LENGTH: 4
<212> TYPE: PRT
<213> ORGANISM: Artificial Sequence
<220> FEATURE:
<223> OTHER INFORMATION: peptide

<400> SEQUENCE: 3

Ser Phe Ser Gln
1

<210> SEQ ID NO 4
<211> LENGTH: 10
<212> TYPE: PRT
<213> ORGANISM: Artificial sequence
<220> FEATURE:
<223> OTHER INFORMATION: peptide

<400> SEQUENCE: 4

Asn Pro Pro Val Leu Lys Arg His Gln Arg
1               5                   10

<210> SEQ ID NO 5
<211> LENGTH: 1457
<212> TYPE: PRT
<213> ORGANISM: Artificial sequence
<220> FEATURE:
<223> OTHER INFORMATION: B-domain deleted recombinant FVIII

<400> SEQUENCE: 5

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Val His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160
```

-continued

```
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
            180                 185                 190
Gly Ala Leu Leu Val Cys Arg Glu Gly Ser Leu Ala Lys Glu Lys Thr
        195                 200                 205
Gln Thr Leu His Lys Phe Ile Leu Leu Phe Ala Val Phe Asp Glu Gly
    210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
```

-continued

```
             580                 585                 590
Ile Leu Phe Ser Val Phe Asp Glu Asn Arg Ser Trp Tyr Leu Thr Glu
             595                 600                 605
Asn Ile Gln Arg Phe Leu Pro Asn Pro Ala Gly Val Gln Leu Glu Asp
             610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                 645                 650                 655
Tyr Ile Leu Ser Ile Gly Ala Gln Thr Asp Phe Leu Ser Val Phe Phe
             660                 665                 670
Ser Gly Tyr Thr Phe Lys His Lys Met Val Tyr Glu Asp Thr Leu Thr
             675                 680                 685
Leu Phe Pro Phe Ser Gly Glu Thr Val Phe Met Ser Met Glu Asn Pro
             690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                 725                 730                 735
Tyr Tyr Glu Asp Ser Tyr Glu Asp Ile Ser Ala Tyr Leu Leu Ser Lys
             740                 745                 750
Asn Asn Ala Ile Glu Pro Arg Ser Phe Ser Gln Asn Pro Pro Val Leu
             755                 760                 765
Lys Arg His Gln Arg Glu Ile Thr Arg Thr Thr Leu Gln Ser Asp Gln
             770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Asn Gln Ser Pro Arg Ser Phe
                 805                 810                 815
Gln Lys Lys Thr Arg His Tyr Phe Ile Ala Ala Val Glu Arg Leu Trp
             820                 825                 830
Asp Tyr Gly Met Ser Ser Ser Pro His Val Leu Arg Asn Arg Ala Gln
             835                 840                 845
Ser Gly Ser Val Pro Gln Phe Lys Lys Val Val Phe Gln Glu Phe Thr
850                 855                 860
Asp Gly Ser Phe Thr Gln Pro Leu Tyr Arg Gly Glu Leu Asn Glu His
865                 870                 875                 880
Leu Gly Leu Leu Gly Pro Tyr Ile Arg Ala Glu Val Glu Asp Asn Ile
                 885                 890                 895
Met Val Thr Phe Arg Asn Gln Ala Ser Arg Pro Tyr Ser Phe Tyr Ser
             900                 905                 910
Ser Leu Ile Ser Tyr Glu Glu Asp Gln Arg Gln Gly Ala Glu Pro Arg
             915                 920                 925
Lys Asn Phe Val Lys Pro Asn Glu Thr Lys Thr Tyr Phe Trp Lys Val
             930                 935                 940
Gln His His Met Ala Pro Thr Lys Asp Glu Phe Asp Cys Lys Ala Trp
945                 950                 955                 960
Ala Tyr Phe Ser Asp Val Asp Leu Glu Lys Asp Val His Ser Gly Leu
                 965                 970                 975
Ile Gly Pro Leu Leu Val Cys His Thr Asn Thr Leu Asn Pro Ala His
             980                 985                 990
Gly Arg Gln Val Thr Val Gln Glu Phe Ala Leu Phe Phe Thr Ile Phe
             995                1000                1005
```

```
Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp
    1220                1225                1230

Gly Lys Lys Trp Gln Thr Tyr Arg Gly Asn Ser Thr Gly Thr Leu
    1235                1240                1245

Met Val Phe Phe Gly Asn Val Asp Ser Ser Gly Ile Lys His Asn
    1250                1255                1260

Ile Phe Asn Pro Pro Ile Ile Ala Arg Tyr Ile Arg Leu His Pro
    1265                1270                1275

Thr His Tyr Ser Ile Arg Ser Thr Leu Arg Met Glu Leu Met Gly
    1280                1285                1290

Cys Asp Leu Asn Ser Cys Ser Met Pro Leu Gly Met Glu Ser Lys
    1295                1300                1305

Ala Ile Ser Asp Ala Gln Ile Thr Ala Ser Ser Tyr Phe Thr Asn
    1310                1315                1320

Met Phe Ala Thr Trp Ser Pro Ser Lys Ala Arg Leu His Leu Gln
    1325                1330                1335

Gly Arg Ser Asn Ala Trp Arg Pro Gln Val Asn Asn Pro Lys Glu
    1340                1345                1350

Trp Leu Gln Val Asp Phe Gln Lys Thr Met Lys Val Thr Gly Val
    1355                1360                1365

Thr Thr Gln Gly Val Lys Ser Leu Leu Thr Ser Met Tyr Val Lys
    1370                1375                1380

Glu Phe Leu Ile Ser Ser Ser Gln Asp Gly His Gln Trp Thr Leu
    1385                1390                1395
```

```
Phe Phe Gln Asn Gly Lys Val Lys Val Phe Gln Gly Asn Gln Asp
    1400                1405                1410

Ser Phe Thr Pro Val Val Asn Ser Leu Asp Pro Pro Leu Leu Thr
    1415                1420                1425

Arg Tyr Leu Arg Ile His Pro Gln Ser Trp Val His Gln Ile Ala
    1430                1435                1440

Leu Arg Met Glu Val Leu Gly Cys Glu Ala Gln Asp Leu Tyr
    1445                1450                1455

<210> SEQ ID NO 6
<211> LENGTH: 1438
<212> TYPE: PRT
<213> ORGANISM: Artificial sequence
<220> FEATURE:
<223> OTHER INFORMATION: B-domain deleted recombinant FVIII

<400> SEQUENCE: 6

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300
```

```
Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
```

```
                    725                 730                 735
Ile Glu Pro Arg Ser Phe Ser Gln Asn Pro Val Leu Lys Arg His
                740                 745                 750
Gln Arg Glu Ile Thr Arg Thr Thr Leu Gln Ser Asp Gln Glu Ile
                755                 760                 765
Asp Tyr Asp Asp Thr Ile Ser Val Glu Met Lys Lys Glu Asp Phe Asp
                770                 775                 780
Ile Tyr Asp Glu Asp Glu Asn Gln Ser Pro Arg Ser Phe Gln Lys Lys
785                 790                 795                 800
Thr Arg His Tyr Phe Ile Ala Ala Val Glu Arg Leu Trp Asp Tyr Gly
                805                 810                 815
Met Ser Ser Ser Pro His Val Leu Arg Asn Arg Ala Gln Ser Gly Ser
                820                 825                 830
Val Pro Gln Phe Lys Lys Val Val Phe Gln Glu Phe Thr Asp Gly Ser
                835                 840                 845
Phe Thr Gln Pro Leu Tyr Arg Gly Glu Leu Asn Glu His Leu Gly Leu
                850                 855                 860
Leu Gly Pro Tyr Ile Arg Ala Glu Val Glu Asp Asn Ile Met Val Thr
865                 870                 875                 880
Phe Arg Asn Gln Ala Ser Arg Pro Tyr Ser Phe Tyr Ser Ser Leu Ile
                885                 890                 895
Ser Tyr Glu Glu Asp Gln Arg Gln Gly Ala Glu Pro Arg Lys Asn Phe
                900                 905                 910
Val Lys Pro Asn Glu Thr Lys Thr Tyr Phe Trp Lys Val Gln His His
                915                 920                 925
Met Ala Pro Thr Lys Asp Glu Phe Asp Cys Lys Ala Trp Ala Tyr Phe
930                 935                 940
Ser Asp Val Asp Leu Glu Lys Asp Val His Ser Gly Leu Ile Gly Pro
945                 950                 955                 960
Leu Leu Val Cys His Thr Asn Thr Leu Asn Pro Ala His Gly Arg Gln
                965                 970                 975
Val Thr Val Gln Glu Phe Ala Leu Phe Phe Thr Ile Phe Asp Glu Thr
                980                 985                 990
Lys Ser Trp Tyr Phe Thr Glu Asn Met Glu Arg Asn Cys Arg Ala Pro
                995                1000                1005
Cys Asn Ile Gln Met Glu Asp Pro Thr Phe Lys Glu Asn Tyr Arg
                1010                1015                1020
Phe His Ala Ile Asn Gly Tyr Ile Met Asp Thr Leu Pro Gly Leu
                1025                1030                1035
Val Met Ala Gln Asp Gln Arg Ile Arg Trp Tyr Leu Leu Ser Met
                1040                1045                1050
Gly Ser Asn Glu Asn Ile His Ser Ile His Phe Ser Gly His Val
                1055                1060                1065
Phe Thr Val Arg Lys Lys Glu Glu Tyr Lys Met Ala Leu Tyr Asn
                1070                1075                1080
Leu Tyr Pro Gly Val Phe Glu Thr Val Glu Met Leu Pro Ser Lys
                1085                1090                1095
Ala Gly Ile Trp Arg Val Glu Cys Leu Ile Gly Glu His Leu His
                1100                1105                1110
Ala Gly Met Ser Thr Leu Phe Leu Val Tyr Ser Asn Lys Cys Gln
                1115                1120                1125
Thr Pro Leu Gly Met Ala Ser Gly His Ile Arg Asp Phe Gln Ile
                1130                1135                1140
```

```
Thr Ala Ser Gly Gln Tyr Gly Gln Trp Ala Pro Lys Leu Ala Arg
        1145            1150            1155
Leu His Tyr Ser Gly Ser Ile Asn Ala Trp Ser Thr Lys Glu Pro
        1160            1165            1170
Phe Ser Trp Ile Lys Val Asp Leu Leu Ala Pro Met Ile Ile His
        1175            1180            1185
Gly Ile Lys Thr Gln Gly Ala Arg Gln Lys Phe Ser Ser Leu Tyr
        1190            1195            1200
Ile Ser Gln Phe Ile Ile Met Tyr Ser Leu Asp Gly Lys Lys Trp
        1205            1210            1215
Gln Thr Tyr Arg Gly Asn Ser Thr Gly Thr Leu Met Val Phe Phe
        1220            1225            1230
Gly Asn Val Asp Ser Ser Gly Ile Lys His Asn Ile Phe Asn Pro
        1235            1240            1245
Pro Ile Ile Ala Arg Tyr Ile Arg Leu His Pro Thr His Tyr Ser
        1250            1255            1260
Ile Arg Ser Thr Leu Arg Met Glu Leu Met Gly Cys Asp Leu Asn
        1265            1270            1275
Ser Cys Ser Met Pro Leu Gly Met Glu Ser Lys Ala Ile Ser Asp
        1280            1285            1290
Ala Gln Ile Thr Ala Ser Ser Tyr Phe Thr Asn Met Phe Ala Thr
        1295            1300            1305
Trp Ser Pro Ser Lys Ala Arg Leu His Leu Gln Gly Arg Ser Asn
        1310            1315            1320
Ala Trp Arg Pro Gln Val Asn Asn Pro Lys Glu Trp Leu Gln Val
        1325            1330            1335
Asp Phe Gln Lys Thr Met Lys Val Thr Gly Val Thr Thr Gln Gly
        1340            1345            1350
Val Lys Ser Leu Leu Thr Ser Met Tyr Val Lys Glu Phe Leu Ile
        1355            1360            1365
Ser Ser Ser Gln Asp Gly His Gln Trp Thr Leu Phe Phe Gln Asn
        1370            1375            1380
Gly Lys Val Lys Val Phe Gln Gly Asn Gln Asp Ser Phe Thr Pro
        1385            1390            1395
Val Val Asn Ser Leu Asp Pro Pro Leu Leu Thr Arg Tyr Leu Arg
        1400            1405            1410
Ile His Pro Gln Ser Trp Val His Gln Ile Ala Leu Arg Met Glu
        1415            1420            1425
Val Leu Gly Cys Glu Ala Gln Asp Leu Tyr
        1430            1435
```

COMPOUNDED MEDIA POWDER FORMULATION AND METHOD OF PREPARATION OF LIQUID MEDIUM FOR CELL CULTURE

CROSS REFERENCE TO RELATED APPLICATIONS

This application is a 371 of International Application No. PCT/US2015/24780, which was filed on Apr. 7, 2015, and which claims the benefit of U.S. Provisional Patent Application No. 61/978,027 filed on Apr. 10, 2014. The contents of each of the above-referenced patent applications are herein incorporated by reference.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One (67,105 Byte ASCII (Text)) file named "SEQUENCE LISTING 15302488 ST25.txt," created on Dec. 15, 2016.

FIELD OF THE INVENTION

The invention relates to the fields of cell biology and cell culture.

BACKGROUND OF THE INVENTION

Various media for growing eukaryotic cells in culture are described in the literature and are commercially available. Cell culture media functions to provide the cells with a suitable pH and osmolality and nutrients essential for cell survival, growth and protein expression.

Examples of some of some common basal culture media are RPMI Media 1640, Medium 199, Minimal Essential Medium (MEM) medium (a "minimal" medium for growth of attached mammalian cells), Leibovitz medium for growth in absence of CO2, Dulbecco's Modified Eagle's Medium and Ham's F12 Medium. The various media are distinguished from one another in that they contain different components in precise amino acids, vitamins, organic salts, trace elements, and other organic compounds which promote the growth of (and protein expression by) the cultured cells.

The development of an optimal cell culture medium is of significant importance, because changes to various components can lead to unexpected improvements in cell growth, increased growth rates, growth to high cell densities, improvements in controlling the stage and amount of cell differentiation, increased protein secretion, increased phenotypic and genetic stability, and elimination of senescence for many cell types, all of which are consequential properties when producing recombinant proteins on a commercial scale.

Preparation of cell culture media, in particular in a commercial setting, is complex, and usually requires the stocking, transfer, preparation and storage of multiple stock solutions and powders and batching in a sequential manner. The large number of process steps and components in media preparation reduce efficiency and increase costs; they can also introduce variability, which in turn can impact the growth of cells and protein production. Hydration is also a significant obstacle to overcome, because as more and more components are added to a media formulation, the more difficult and less predictable it becomes to completely hydrate and dissolve the components to achieve a homogeneous mixture and an optimal osmolality, due to the richness and complexity of the composition, and interactions amongst the various components. For this reason, some components are often hydrated separately in complex media formulations. However, this results in increased cost and complexity during production.

Accordingly, there remains a need in the art for improved/further compounded dry media powder (DMP) formulations and methods of making the same in order to reduce complexity and lower costs while maintaining the correct composition in the fully hydrated liquid media as well as similar cell culture performance and recombinant protein production.

SUMMARY OF THE INVENTION

In one aspect, the invention provides a compounded cell culture medium powder formulation comprising: a basal medium powder and a cell culture media supplement, wherein the cell culture media supplement comprises: one or more salts; one or more growth factors; one or more inorganic ions; an amino acid supplement comprising one or more of asparagine, glutamine, histidine, and serine; one or more buffers; and one or more anti-foaming agents.

In some embodiments, the basal medium powder comprises Dulbecco's Modified Eagle's Medium, Ham's Medium F12, Eagle's Minimal Essential Medium, RPMI 1640 Medium, Dulbecco's Modified Eagle's Medium/Ham's F12 Medium (DMEM/F-12; 1:1 ratio), and combinations or modifications thereof.

In some embodiments, the basal medium powder comprises one or more of the following components or a combination thereof: biotin, calcium chloride, choline chloride, cyanocobalamin (B12), D+ mannose, D-calcium pantothenate, dextrose (anhydrous), DL-alpha-lipoic acid, ferric nitrate 9H2O, ferrous sulfate 7H2O, folic acid, glycine, hypoxanthine, I-inositol, L-alanine, L-arginine, L-asparagine, L-aspartic acid, L-cysteine HCl H2O, L-cystine 2HCl, L-glutamic acid (anhydrous), L-glutamine, L-glutathione, L-histidine FB, L-histidine HCl, L-isoleucine, L-leucine, L-lysine, L-methionine, L-phenylaline, L-proline, L-serine, L-threonine, L-tryptophan, L-tyrosine, L-valine, magnesium chloride, magnesium sulfate anhydrous, niacinamide, O-phosphoryl-ethanolamine, potassium chloride, putrescine 2HCl, pyridoxal HCl, pyridoxine HCl, riboflavin, sodium chloride, sodium phosphate monobasic H2O, sodium phosphate dibasic anhydrous, sodium pyruvate, thiamine HCl, thymidine, zinc sulfate 7H2O, cupric sulfate, selenium dioxide, linoleic acid, beta-mercaptoethanol and ethanolamine free-base FB.

In some embodiments, the basal medium powder has a concentration of 8-30 g/L when the compounded cell culture medium powder formulation is combined with water to form a cell culture medium. In some embodiments, the basal medium powder has a concentration of 12-14 g/L when the compounded cell culture medium powder formulation is combined with water to form a cell culture medium. In some embodiments, the basal medium powder has a concentration of about 13 g/L when the compounded cell culture medium powder formulation is combined with water to form a cell culture medium.

In some embodiments, the compounded cell culture medium powder formulation further comprises a pH indicator. In some embodiments, the pH indicator is Phenol Red Na, wherein the Phenol Red Na is present at a concentration of about 0.001 to about 0.02 g/L when the compounded cell culture medium powder formulation is combined with water to form a cell culture medium. In some embodiments, the Phenol Red Na is present at a concentration of about 0.0069 g/L when the compounded cell culture medium powder formulation is combined with water to form a cell culture medium.

In some embodiments, the basal medium powder components provide the following final concentration upon hydration to form a cell culture medium:
  i) 0.0003-0.003 g/L biotin;
  ii) 0.035-0.33 g/L calcium chloride;
  iii) 0.003-0.03 g/L choline chloride;
  iv) 0.0002-0.002 g/L cyanocobalamin (B12);
  v) 1-10 g/L D+ mannose;
  vi) 0.001-0.01 g/L D-calcium pantothenate;
  vii) 0.3-3.0 g/L dextrose (anhydrous);
  viii) 0.00003-0.0003 g/L DL-alpha-lipoic acid;
  ix) 0.00002-0.00015 g/L ferric nitrate $9H_2O$;
  x) 0.0001-0.0015 g/L ferrous sulfate $7H_2O$;
  xi) 0.001-0.01 g/L folic acid;
  xii) 0.007-0.20 g/L glycine;
  xiii) 0.001-0.01 g/L hypoxanthine 2Na;
  xiv) 0.005-0.05 g/L I-inositol;
  xv) 0.003-0.03 g/L L-alanine;
  xvi) 0.08-1.4 g/L L-arginine;
  xvii) 0.006-0.16 g/L L-asparagine;
  xviii) 0.005-0.10 g/L L-aspartic acid;
  xix) 0.005-0.05 g/L L-cysteine HCl $H_2O$;
  xx) 0.02-0.2 g/L L-cystine 2HCl;
  xxi) 0.005-0.15 g/L L-glutamic acid (anhydrous);
  xxii) 0.02-1.5 g/L L-glutamine;
  xxiii) 0.0003-0.003 g/L L-glutathione;
  xxiv) 0.02-0.2 g/L L-histidine HCl;
  xxv) 0.03-0.9 g/L L-isoleucine;
  xxvi) 0.03-0.9 g/L L-leucine;
  xxvii) 0.05-1.5 g/L L-lysine;
  xxviii) 0.01-0.3 g/L L-methionine;
  xxix) 0.02-0.6 g/L L-phenylaline;
  xxx) 0.008-0.25 g/L L-proline;
  xxxi) 0.009-0.25 g/L L-serine;
  xxxii) 0.03-0.9 g/L L-threonine;
  xxxiii) 0.006-0.16 g/L L-tryptophan;
  xxxiv) 0.03-0.9 g/L L-tyrosine 2Na $2H_2O$;
  xxxv) 0.03-0.9 g/L L-valine;
  xxxvi) 0.01-0.18 g/L magnesium chloride;
  xxxvii) 0.02-0.12 g/L magnesium sulfate anhydrous;
  xxxviii) 0.001-0.01 g/L niacinamide;
  xxxix) 0.0005-0.005 g/L O-phoshphoryl-ethanolamine;
  xl) 0.1-1.0 g/L potassium chloride;
  xli) 0.00002-0.0002 g/L putrescine 2HCl;
  xlii) 0.001-0.01 g/L pyridoxal HCl;
  xliii) 0.00001-0.0001 g/L pyridoxine HCl,
  xliv) 0.0001-0.001 g/L riboflavin,
  xlv) 2.0-15 g/L sodium chloride,
  xlvi) 0.02-0.2 g/L sodium phosphate monobasic $H_2O$,
  xlvii) 0.02-0.2 g/L sodium phosphate dibasic anhydrous,
  xlviii) 0.015-0.15 g/L sodium pyruvate,
  xlix) 0.001-0.01 g/L thiamine HCl,
  l) 0.0001-0.001 g/L thymidine,
  li) 0.00015-0.0015 g/L zinc sulfate $7H_2O$,
  lii) 0.0000006-0.000006 g/L cupric sulfate $5H_2O$,
  liii) 0.0000005-0.000008 g/L selenium dioxide,
  liv) 0.00001-0.0001 g/L linoleic acid,
  lv) 0.0001-0.001 g/L beta-mercaptoethanol; and
  lvi) 0.0003-0.005 g/L ethanolamine FB.

In some embodiments, the basal medium powder components provide the following final concentration upon hydration to form a cell culture medium:
  i) about 0.001 g/L biotin;
  ii) about 0.11665 g/L calcium chloride;
  iii) about 0.00998 g/L choline chloride;
  iv) about 0.00068 g/L cyanocobalamin (B 12);
  v) about 3 g/L D+ mannose;
  vi) about 0.00312 g/L D-calcium pantothenate;
  vii) about 1 g/L dextrose (anhydrous);
  viii) about 0.000103 g/L DL-alpha-lipoic acid;
  ix) about 0.00005 g/L ferric nitrate $9H_2O$;
  x) about 0.000417 g/L ferrous sulfate $7H_2O$;
  xi) about 0.00366 g/L folic acid;
  xii) about 0.02626 g/L glycine;
  xiii) about 0.0027 g/L hypoxanthine 2Na;
  xiv) about 0.01451 g/L I-inositol;
  xv) about 0.01336 g/L L-alanine;
  xvi) about 0.27435 g/L L-arginine;
  xvii) about 0.0225 g/L L-asparagine;
  xviii) about 0.01995 g/L L-aspartic acid;
  xix) about 0.01756 g/L L-cysteine HCl $H_2O$;
  xx) about 0.06256 g/L L-cystine 2HCl;
  xxi) about 0.02206 g/L L-glutamic acid (anhydrous);
  xxii) about 0.73 g/L L-glutamine;
  xxiii) about 0.001 g/L L-glutathione;
  xxiv) about 0.07348 g/L L-histidine HCl;
  xxv) about 0.1057 g/L L-isoleucine;
  xxvi) about 0.11096 g/L L-leucine;
  xxvii) about 0.16385 g/L L-lysine;
  xxviii) about 0.03224 g/L L-methionine;
  xxix) about 0.06748 g/L L-phenylaline;
  xxx) about 0.02875 g/L L-proline;
  xxxi) about 0.03676 g/L L-serine;
  xxxii) about 0.10156 g/L L-threonine;
  xxxiii) about 0.01902 g/L L-tryptophan;
  xxxiv) about 0.10771 g/L L-tyrosine 2Na $2H_2O$;
  xxxv) about 0.09866 g/L L-valine;
  xxxvi) about 0.028 g/L magnesium chloride;
  xxxvii) about 0.04884 g/L magnesium sulfate anhydrous;
  xxxviii) about 0.00302 g/L niacinamide;
  xxxix) about 0.0014 g/L O-phoshphoryl-ethanolamine;
  xl) about 0.31182 g/L potassium chloride;
  xli) about 0.000081 g/L putrescine 2HCl;
  xlii) about 0.003 g/L pyridoxal HCl;
  xliii) about 0.000031 g/L pyridoxine HCl,
  xliv) about 0.000319 g/L riboflavin,
  xlv) about 6.1234 g/L sodium chloride,
  xlvi) about 0.0625 g/L sodium phosphate monobasic $H_2O$,
  xlvii) about 0.07099 g/L sodium phosphate dibasic anhydrous,
  xlviii) about 0.055 sodium pyruvate,
  xlix) about 0.00317 g/L thiamine HCl,
  l) about 0.000364 g/L thymidine,
  li) about 0.000432 g/L zinc sulfate $7H_2O$,
  lii) about 0.00000125 g/L cupric sulfate $5H_2O$,
  liii) about 0.00000222 g/L selenium dioxide,
  liv) about 0.000042 g/L linoleic acid,
  lv) about 0.00039065 g/L beta-mercaptoethanol; and
  lvi) about 0.0012 g/L ethanolamine FB.

In some embodiments, the one or more salts of the cell culture media supplement comprises magnesium chloride in a concentration of 0.5-5 g/L upon hydration to form a cell culture medium. In some embodiments, the magnesium chloride has a concentration of about 1.428 g/L upon hydration to form a cell culture medium.

In some embodiments, the cell culture media supplement comprises recombinant insulin as a growth factor. In some embodiments, the insulin has a concentration of 0.5-15 mg/L upon hydration to form a cell culture medium. In some embodiments, the insulin has a concentration of about 3 mg/L upon hydration to form a cell culture medium.

In some embodiments, the one or more inorganic ions of the cell culture media supplement comprises trace metals selected ammonium molybdate, chromium potassium sulfate, cupric sulfate, lithium chloride, manganese sulfate, sodium metasilicate and combinations thereof. In some embodiments, the ammonium molybdate is ammonium molybdate 4H2O; the chromium potassium sulfate is chromium potassium sulfate 12H2O, the cupric sulfate is cupric sulfate 5H2O, the lithium chloride is lithium chloride (anhydrous), the manganese sulfate is manganese sulfate H2O and the sodium metasilicate is sodium metasilicate 9H2O.

In some embodiments, the trace metals provide the following final concentration upon hydration to form a cell culture medium:
  i) 0.0005-0.01 mg/L of ammonium molybdate $4H_2O$;
  ii) 0.0001-0.01 mg/L of chromium potassium sulfate $12H_2O$;
  iii) 0.001-0.125 mg/L of cupric sulfate $5H_2O$;
  iv) 0.001-0.1 mg/L of lithium chloride (anhydrous);
  v) 0.00004-0.004 mg/L of manganese sulfate $H_2O$; and
  vi) 0.04-4.2 mg/L of sodium metasilicate $9H_2O$.

In some embodiments, the cell culture media supplement comprises a combination of ammonium molybdate 4H2O, chromium potassium sulfate 12H2O, cupric sulfate 5H2O, lithium chloride (anhydrous), manganese sulfate H2O, and sodium metasilicate 9H2O. In some embodiments, the trace metals provide the following final concentration upon hydration to form a cell culture medium:
  i) about 0.0037 mg/L of ammonium molybdate $4H_2O$;
  ii) about 0.001 mg/L of chromium potassium sulfate $12H_2O$;
  iii) about 0.0125 mg/L of cupric sulfate $5H_2O$;
  iv) about 0.01 mg/L of lithium chloride (anhydrous);
  v) about 0.000452 mg/L of manganese sulfate $H_2O$; and
  vi) about 0.4263 mg/L of sodium metasilicate $9H_2O$.

In some embodiments, the amino acid supplement of the cell culture media supplement comprises a combination of asparagine H2O, glutamine, histidine, and serine. In some embodiments, the amino acid supplement has the following final concentration upon hydration to form a cell culture medium:
  i) 0.007-0.07 g/L asparagine $H_2O$;
  ii) 0.25-2.5 g/L glutamine;
  iii) 0.5-5.0 g/L histidine, free base; and
  iv) 0.01-0.1 g/L serine.

In some embodiments, the amino acid supplement has the following final concentration upon hydration to form a cell culture medium:
  i) about 0.0225 g/L asparagine $H_2O$;
  ii) about 0.73 g/L glutamine;
  iii) about 1.552 g/L histidine; and
  iv) about 0.03676 g/L serine.

In some embodiments, the one or more buffers of the cell culture media supplement is selected from the group consisting of 3-(N-morpholino)propanesulfonic acid (MOPS) free acid, 3-(N-morpholino)propanesulfonic acid (MOPS) Na, hydroxyethyl piperazineethanesulfonic acid (HEPES) and sodium bicarbonate. In some embodiments, the formulation comprises a combination of MOPS free acid and MOPS Na. In some embodiments, the buffers provide the following final concentration upon hydration to form a cell culture medium:
  i) 0.3-3 g/L MOPS free acid; and
  ii) 1.0-10 g/L MOPS Na.

In some embodiments, the anti-foaming agent of the cell culture media supplement comprises a polyol copolymer based on ethylene oxide and propylene oxide. In some embodiments, the anti-foaming agent is Pluronic F68. In some embodiments, the Pluronic F68 has a concentration of 0.1-10 g/L upon hydration to form a cell culture medium. In some embodiments, the Pluronic F68 has a concentration of about 1 g/L upon hydration to form a cell culture medium.

In another aspect, the invention provides a method of making the compounded cell culture medium powder formulation of the invention, comprising combining the basal medium powder; one or more salts; one or more growth factors; one or more inorganic ions; an amino acid supplement comprising one or more of asparagine, glutamine, histidine, and serine; one or more buffers; and one or more anti-foaming agents.

In another aspect, the invention provides a method of making a cell culture medium for growing mammalian cells, comprising contacting the compounded cell culture medium powder formulation with water, thereby making a cell culture medium for growing mammalian cells. In some embodiments, the components are substantially dissolved in the water. In some embodiments, the method further comprises combining a solution comprising $FeSO_4$ $7H_2O$ and a chelating agent. In some embodiments, the chelating agent is ethylenediaminetetraacetic acid (EDTA). In some embodiments, the $FeSO_4$ $7H_2O$ and EDTA have the following final concentration in the cell culture medium: 0.004-0.04 g/L $FeSO_4$ $7H_2O$; and 0.006-0.06 g/L EDTA. In some embodiments, the $FeSO_4$ $7H_2O$ and EDTA have the following final concentration in the cell culture medium: about 0.0138 g/L $FeSO_4$ $7H_2O$; and about 0.018625 g/L EDTA.

In another embodiment, the method further comprises contacting the cell culture medium of the invention with cells. In some embodiments, the cells are mammalian cells.

In another embodiment, the invention provides a method of culturing cells, comprising, comprising contacting cells with a cell culture medium of the invention and culturing the cells in the medium for a period of time.

In another embodiment, the invention provides a method of producing a protein of interest, comprising contacting cells expressing the protein of interest with a cell culture medium; culturing the cells in the medium for a period of time; and isolating the protein of interest from the cell culture medium.

In some embodiments, the mammalian cells are selected from the group consisting of Chinese Hamster Ovary (CHO) cells, DP12 CHO cells, DG44 CHO cells, Human Embryonic Kidney (HEK) cells, HEK 293 cells, and baby hamster kidney (BHK) cells. In some embodiments, the mammalian cells recombinantly express a protein of interest. In some embodiments, the protein of interest is selected from the group consisting of coagulation Factor VIII (FVIII), variants and fragments thereof. In some embodiments, the FVIII is selected from wild-type FVIII, B-domain deleted FVIII and FVIII conjugated with a biocompatible polymer. In some embodiments, the biocompatible polymer is polyethylene glycol (PEG). In some embodiments, the PEG is covalently attached to the polypeptide at one or more of the factor VIII amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION OF THE INVENTION

Figure 1:
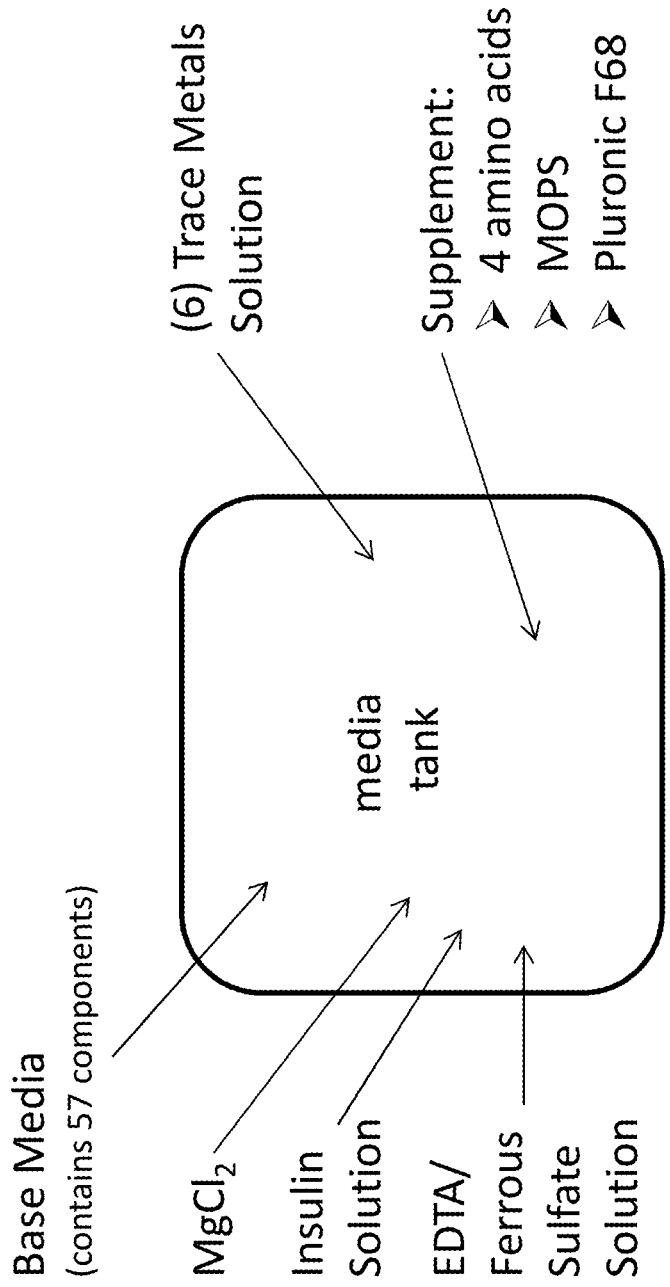
FIG. 1. Illustration of non-compounded media preparation. Most (e.g., 57) medium components are contained in the Base Media powder, which can be premixed. Additional media components are added separately to their respective target final concentration to complete the formulation. $FeSO_4$/EDTA, Trace Metals Panel, and rH insulin are prepared as stock solutions and added to media batches as liquids while magnesium chloride and the supplement are added as powders. The complete medium contains basic cell nutrients, salts, carbohydrates, anti-shear factors, amino acids, vitamins, trace metals, insulin and various other chemicals that aid in cell growth and recombinant protein production and stabilize the recombinant protein product secreted from the cell.
Figure 2:
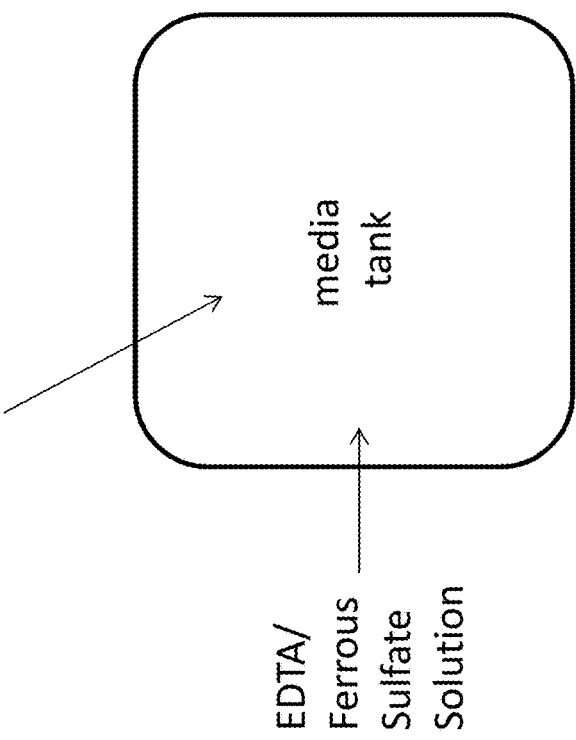
FIG. 2. Illustration of cell culture media preparation using a (nearly fully-compounded) termed herein as "compounded" formulation. Ferrous sulfate/EDTA is not capable of compounding, apparently due to unintended chelation of other bivalent trace metals (existing in the medium) by the EDTA and is therefore added separately.

The present inventor has developed a compounded cell culture medium powder formulation useful for making a cell culture medium and for recombinant protein production. Described herein are formulations of compounded mammalian cell culture medium powder, methods of making the same and a hydration method which can reduce cost, simplify workflow, and reduce complexity of medium preparation—all which are especially important in commercial settings, among other advantages described herein.

For the purpose of interpreting this specification, the following definitions will apply and whenever appropriate, terms used in the singular will also include the plural and vice versa.

In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Unless defined otherwise, all technical and scientific terms used herein have the same meaning as commonly understood by those of ordinary skill in the art to which this invention pertains. The following references provide one of skill with a general definition of many of the terms used in this invention: Academic Press Dictionary of Science and Technology, Morris (Ed.), Academic Press (1st ed., 1992); Oxford Dictionary of Biochemistry and Molecular Biology, Smith et al. (Eds.), Oxford University Press (revised ed., 2000); Encyclopaedic Dictionary of Chemistry, Kumar (Ed.), Anmol Publications Pvt. Ltd. (2002); Dictionary of Microbiology and Molecular Biology, Singleton et al. (Eds.), John Wiley & Sons (3rd ed., 2002); Dictionary of Chemistry, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Practitioners are also directed to Sambrook et al. (1989) *Molecular Cloning: A Laboratory Manual* (*Second Edition*), Cold Spring Harbor Press, Plainview, N.Y.; Ausubel F M et al. (1993) and *Current Protocols in Molecular Biology*, John Wiley & Sons, New York, N.Y.; and Gelvin and Schilperoot, eds. (1997), for definitions and terms of the art. Further clarifications of some of these terms as they apply specifically to this invention are provided herein.

The term "about" with respect to the compositions means plus or minus a range of up to 20%.

As used herein, the terms "cell," "cells," "cell line," "host cell," and "host cells," are used interchangeably and, encompass plant and animal cells and include invertebrate, non-mammalian vertebrate and mammalian cells. All such designations include cell populations and progeny. Thus, the terms "transformants" and "transfectants" include the primary subject cell and cell lines derived therefrom without regard for the number of transfers. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and *Bombyx mori* cells. See, e.g., Luckow et al., *Bio/Technology* 6:47-55 (1988). The cells may be differentiated, partially differentiated or undifferentiated, e.g. stem cells, including embryonic stem cells and pluripotent stem cells. Additionally tissue samples derived from organs or organ systems may be used according to the invention.

The terms "cell culture," or "tissue culture" refer to cells grown in suspension or grown adhered to a variety of surfaces or substrates in vessels such as roller bottles, tissue culture flasks, dishes, multi-well plates and the like. Large scale approaches, such as bioreactors, including adherent cells growing attached to microcarriers in stirred fermentors, are also encompassed by the term "cell culture." Moreover, it is possible not only to culture contact-dependent cells, but also to use suspension culture techniques in the methods of the claimed invention. Exemplary microcarriers include, for example, dextran, collagen, plastic, gelatin and cellulose and others as described in Butler, Spier & Griffiths, *Animal cell Biotechnology* 3:283-303 (1988). Porous carriers, such as, for example, Cytoline™ or Cytopore™, as well as dextran-based carriers, such as DEAE-dextran (Cytodex 1™ quaternary amine-coated dextran (Cytodex™) or gelatin-based carriers, such as gelatin-coated dextran (Cytodex 3™) may also be used. Cell culture procedures for both large and small-scale production of proteins are encompassed by the present invention. Procedures including, but not limited to, a fluidized bed bioreactor, hollow fiber bioreactor, roller bottle culture, or stirred tank bioreactor system may be used, with or without microcarriers, and operated alternatively in a batch, fed-batch, or perfusion mode.

The term "mammalian host cell," "mammalian cell," "mammalian recombinant host cell," and the like, refer to cell lines derived from mammals that are capable of growth and survival when placed in either monolayer culture or in suspension culture in a medium containing the appropriate nutrients and growth factors. Exemplary mammalian cells include, for example, cells derived from human, non-human primate, cat, dog, sheep, goat, cow, horse, pig, rabbit, rodents including mouse, hamster, rat and guinea pig and any derivatives and progenies thereof. Typically, the cells are capable of expressing and secreting large quantities of a particular protein of interest (typically a recombinant protein) into the culture medium, and are cultured for this purpose. However, the cells may be cultured for a variety of other purposes as well, and the scope of this invention is not limited to culturing the cells only for production of recombinant proteins. Examples of suitable mammalian cell lines, capable of growth in the media of this invention, include monkey kidney CVI line transformed by SV40 (COS-7, ATCC®CRL 1651); human embryonic kidney line 293S (Graham et al., *J. Gen. Virolo.*, 36:59 (1977)); baby hamster kidney cells (BHK, ATCC® CCL 10); mouse sertoli cells (TM4, Mather, *Biol. Reprod.*, 23:243 (1980)); monkey kidney cells (CVI-76, ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor cells (MMT 060562, ATCC® CCL SI); rat hepatoma cells (HTC, MI.54, Baumann et al., *J. Cell Biol.*, 85:1 (1980)); and TR-1 cells (Mather et al., *Annals N.Y. Acad. Sci.*, 383:44 (1982)) and hybridoma cell lines. In some embodiments, Chinese hamster ovary cells (Urlab and Chasin, *Proc. Natl. Acad. Sci. USA*, 77:4216 (1980)) can be grown in the media. CHO cells suitable for use in the methods of the present invention have also been described in the following documents: EP 117,159, published Aug. 29, 1989; U.S. Pat. Nos. 4,766,075; 4,853,330; 5,185,259; Lubiniecki et al., in *Advances in Animal Cell Biology and Technology for Bioprocesses*, Spier et al., eds. (1989), pp. 442-451. Known CHO derivatives suitable for use herein include, for example, CHO/-DHFR (Urlaub and Chasin, *Proc. Natl. Acad. Sci. USA*, 77: 4216 (1980)), CHO-K1 DUX B11 (Simonsen and Levinson, *Proc. Natl. Acad. Sci. USA* 80: 2495-2499 (1983); Urlaub and Chasin, supra), and dp 12.CHO cells (EP 307,247 published Mar. 15, 1989). In one embodiment, the cells useful for growth in the media are selected form Chinese Hamster Ovary (CHO) cells, DP12 CHO cells, DG44 CHO cells, Human Embryonic Kidney (HEK) cells, HEK 293 cells, and baby hamster kidney (BHK) cells. In some embodiments, the cells express a protein or proteins of interest. In some embodiments, the cells have been engineered to recombinantly express the protein.

In one embodiment, the invention provides a compounded cell culture medium powder formulation comprising a basal medium powder and a cell culture media supplement, wherein the cell culture media supplement comprises one or more salts; one or more growth factors; one or more inorganic ions; an amino acid supplement comprising one or more of asparagine, glutamine, histidine, and serine; one or more buffers; and one or more anti-foaming agents.

The compounded cell culture medium powder formulation is generally for use as a cell culture medium which is "serum free" wherein the medium is essentially free of serum from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

Notwithstanding, the compounded cell culture dry powder medium described in the present invention can also be used in formulations where serum from various sources and/or animals and/or combinations or derivatives thereof (e.g., FBS or human plasma protein-fraction solution, HPPS, and/or the like), is/are added to generate the final formulation for cultivating cells.

The term "basal medium powder" or "basal media" refers to cell culture media that may contain, for example, any or all of the following components: proteins, lipids, carbohydrates, amino acids, organic and/or inorganic salts, buffers (e.g., bicarbonate), vitamins, hormones, antibiotics, and pH indicators (e.g., phenol red). Examples of cell culture media bases that can be used in accordance with the present invention are not limiting and can include: Dulbecco's Modified Eagle's Medium (DMEM), Ham's F12 Medium, MCDB Media, Minimum Essential Medium Eagle, RPMI Media, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, and William's Medium E. In some embodiments, the basal medium powder is a combination or a modification of the above listed cell culture media bases. In some embodiments, the basal media powder is Dulbecco's Modified Eagle's Medium/Ham's F12 Medium (DMEM/F-12; 1:1 ratio).

In some embodiments, the basal medium powder comprises one or more of the following components or a combination thereof: biotin, calcium chloride, choline chloride, cyanocobalamin (B12), D+ mannose, D-calcium pantothenate, dextrose (anhydrous), DL-alpha-lipoic acid, ferric nitrate $9H_2O$, ferrous sulfate $7H_2O$, folic acid, glycine, hypoxanthine, I-inositol, L-alanine, L-arginine, L-asparagine, L-aspartic acid, L-cysteine HCl $H_2O$, L-cystine 2HCl, L-glutamic acid (anhydrous), L-glutamine, L-glutathione, L-histidine FB, L-histidine HCl, L-isoleucine, L-leucine, L-lysine, L-methionine, L-phenylaline, L-proline, L-serine, L-threonine, L-tryptophan, L-tyrosine, L-valine, magnesium chloride, magnesium sulfate anhydrous, niacinamide, O-phosphoryl-ethanolamine, potassium chloride, putrescine 2HCl, pyridoxal HCl, pyridoxine HCl, riboflavin, sodium chloride, sodium phosphate monobasic $H_2O$, sodium phosphate dibasic anhydrous, sodium pyruvate, thiamine HCl, thymidine, zinc sulfate $7H_2O$, cupric sulfate, selenium dioxide, linoleic acid, beta-mercaptoethanol and ethanolamine free-base FB.

Cell culture media components are generally available from the following sources: Research Organics Inc., United Biochemicals, Angus Chemical Company, (Mikrochem) Bayer Biotechnology, Kyowa Hakko U.S.A. Inc., Ferro/Pfanstiehl, Sigma-Aldrich Inc., Research Organics Inc., VWR Scientific Inc., Ajinomoto AminoScience LLC, EMD MILLIPORE CORPORATION, Kyowa Hakko U.S.A. Inc., and Tilley Chemical Co., Inc.

In some embodiments, the compounded cell culture medium powder formulation comprises a pH indicator. The pH indicator is not limiting, provided that it is suitable for cell culture. In some embodiments, the pH indicator is Phenol Red Na. In some embodiments, Phenol Red Na is present at a concentration of about 0.001 to about 0.02 g/L when the compounded cell culture medium powder formulation is combined with water to form a cell culture medium. In some embodiments, the Phenol Red Na is present at a concentration of about 0.0069 g/L.

In some embodiments, the basal medium powder comprises the following components which provide the following final concentration upon hydration to form a cell culture medium:
i) 0.0003-0.003 g/L biotin;
ii) 0.035-0.33 g/L calcium chloride;
iii) 0.003-0.03 g/L choline chloride;
iv) 0.0002-0.002 g/L cyanocobalamin (B12);
v) 1-10 g/L D+ mannose;
vi) 0.001-0.01 g/L D-calcium pantothenate;
vii) 0.3-3.0 g/L dextrose (anhydrous);
viii) 0.00003-0.0003 g/L DL-alpha-lipoic acid;
ix) 0.00002-0.00015 g/L ferric nitrate $9H_2O$;
x) 0.0001-0.0015 g/L ferrous sulfate $7H_2O$;
xi) 0.001-0.01 g/L folic acid;
xii) 0.007-0.20 g/L glycine;
xiii) 0.001-0.01 g/L hypoxanthine 2Na;
xiv) 0.005-0.05 g/L I-inositol;
xv) 0.003-0.03 g/L L-alanine;
xvi) 0.08-1.4 g/L L-arginine;
xvii) 0.006-0.16 g/L L-asparagine;
xviii) 0.005-0.10 g/L L-aspartic acid;
xix) 0.005-0.05 g/L L-cysteine HCl $H_2O$;
xx) 0.02-0.2 g/L L-cystine 2HCl;
xxi) 0.005-0.15 g/L L-glutamic acid (anhydrous);
xxii) 0.02-1.5 g/L L-glutamine;
xxiii) 0.0003-0.003 g/L L-glutathione;
xxiv) 0.02-0.2 g/L L-histidine HCl;
xxv) 0.03-0.9 g/L L-isoleucine;
xxvi) 0.03-0.9 g/L L-leucine;
xxvii) 0.05-1.5 g/L L-lysine;
xxviii) 0.01-0.3 g/L L-methionine;
xxix) 0.02-0.6 g/L L-phenylaline;
xxx) 0.008-0.25 g/L L-proline;
xxxi) 0.009-0.25 g/L L-serine;
xxxii) 0.03-0.9 g/L L-threonine;
xxxiii) 0.006-0.16 g/L L-tryptophan;
xxxiv) 0.03-0.9 g/L L-tyrosine 2Na $2H_2O$;
xxxv) 0.03-0.9 g/L L-valine;
xxxvi) 0.01-0.18 g/L magnesium chloride;
xxxvii) 0.02-0.12 g/L magnesium sulfate anhydrous;
xxxviii) 0.001-0.01 g/L niacinamide;
xxxix) 0.0005-0.005 g/L O-phoshphoryl-ethanolamine;
xl) 0.1-1.0 g/L potassium chloride;
xli) 0.00002-0.0002 g/L putrescine 2HCl;
xlii) 0.001-0.01 g/L pyridoxal HCl;
xliii) 0.00001-0.0001 g/L pyridoxine HCl,
xliv) 0.0001-0.001 g/L riboflavin,
xlv) 2.0-15 g/L sodium chloride,
xlvi) 0.02-0.2 g/L sodium phosphate monobasic $H_2O$,
xlvii) 0.02-0.2 g/L sodium phosphate dibasic anhydrous,
xlviii) 0.015-0.15 g/L sodium pyruvate,
xlix) 0.001-0.01 g/L thiamine HCl,
l) 0.0001-0.001 g/L thymidine,
li) 0.00015-0.0015 g/L zinc sulfate $7H_2O$,
lii) 0.0000006-0.000006 g/L cupric sulfate $5H_2O$,
liii) 0.0000005-0.000008 g/L selenium dioxide,
liv) 0.00001-0.0001 g/L linoleic acid,
lv) 0.0001-0.001 g/L beta-mercaptoethanol; and
lvi) 0.0003-0.005 g/L ethanolamine FB.

In some embodiments, the basal medium powder comprises the following components which provide the following final concentration upon hydration to form a cell culture medium:
i) about 0.001 g/L biotin;
ii) about 0.11665 g/L calcium chloride;
iii) about 0.00998 g/L choline chloride;
iv) about 0.00068 g/L cyanocobalamin (B12);
v) about 3 g/L D+ mannose;
vi) about 0.00312 g/L D-calcium pantothenate;
vii) about 1 g/L dextrose (anhydrous);
viii) about 0.000103 g/L DL-alpha-lipoic acid;
ix) about 0.00005 g/L ferric nitrate $9H_2O$;
x) about 0.000417 g/L ferrous sulfate $7H_2O$;
xi) about 0.00366 g/L folic acid;
xii) about 0.02626 g/L glycine;
xiii) about 0.0027 g/L hypoxanthine 2Na;
xiv) about 0.01451 g/L I-inositol;
xv) about 0.01336 g/L L-alanine;
xvi) about 0.27435 g/L L-arginine;
xvii) about 0.0225 g/L L-asparagine;
xviii) about 0.01995 g/L L-aspartic acid;
xix) about 0.01756 g/L L-cysteine HCl $H_2O$;
xx) about 0.06256 g/L L-cystine 2HCl;
xxi) about 0.02206 g/L L-glutamic acid (anhydrous);
xxii) about 0.73 g/L L-glutamine;
xxiii) about 0.001 g/L L-glutathione;
xxiv) about 0.07348 g/L L-histidine HCl;
xxv) about 0.1057 g/L L-isoleucine;
xxvi) about 0.11096 g/L L-leucine;
xxvii) about 0.16385 g/L L-lysine;
xxviii) about 0.03224 g/L L-methionine;
xxix) about 0.06748 g/L L-phenylaline;
xxx) about 0.02875 g/L L-proline;
xxxi) about 0.03676 g/L L-serine;
xxxii) about 0.10156 g/L L-threonine;
xxxiii) about 0.01902 g/L L-tryptophan;
xxxiv) about 0.10771 g/L L-tyrosine 2Na $2H_2O$;
xxxv) about 0.09866 g/L L-valine;
xxxvi) about 0.028 g/L magnesium chloride;
xxxvii) about 0.04884 g/L magnesium sulfate anhydrous;
xxxviii) about 0.00302 g/L niacinamide;
xxxix) about 0.0014 g/L O-phoshphoryl-ethanolamine;
xl) about 0.31182 g/L potassium chloride;
xli) about 0.000081 g/L putrescine 2HCl;
xlii) about 0.003 g/L pyridoxal HCl;
xliii) about 0.000031 g/L pyridoxine HCl,
xliv) about 0.000319 g/L riboflavin,
xlv) about 6.1234 g/L sodium chloride,
xlvi) about 0.0625 g/L sodium phosphate monobasic $H_2O$, xlvii) about 0.07099 g/L sodium phosphate dibasic anhydrous,
xlviii) about 0.055 sodium pyruvate,
xlix) about 0.00317 g/L thiamine HCl,
l) about 0.000364 g/L thymidine,
li) about 0.000432 g/L zinc sulfate 7H$_2$O,
lii) about 0.00000125 g/L cupric sulfate 5H$_2$O,
liii) about 0.00000222 g/L selenium dioxide,
liv) about 0.000042 g/L linoleic acid,
lv) about 0.00039065 g/L beta-mercaptoethanol; and
lvi) about 0.0012 g/L ethanolamine FB.

The components that can be used in the compounded media formulation as discussed herein can be in an anhydrous or in a hydrated form, and many such anhydrous and hydrated forms of the components are known by persons skilled in the art. For example, as indicated above, in some embodiments, the composition comprises hydrated forms of cupric sulfate, zinc sulfate, sodium phosphate monobasic, L-tyrosine, L-cysteine, ferric nitrate, and ferrous sulfate. Each of these components can be substituted with anhydrous forms, and the concentration ranges can be recalculated based on differences in molecular weight between the hydrated and anhydrous forms. Likewise, any anhydrous forms mentioned in the specification can be substituted with hydrated forms, and the concentration ranges recalculated accordingly.

In some embodiments, the basal medium powder has a concentration of 8-30 g/L upon hydration to form a cell culture medium. In some embodiments, the basal medium powder has a concentration of 12-14 g/L upon hydration to form a cell culture medium. In some embodiments, the basal medium powder has a concentration of about 13 g/L upon hydration to form a cell culture medium.

The one or more salts of the cell culture media supplement is not limiting and includes any salts, and hydration state thereof, which are suitable for use in cell culture. In some embodiments, the one or more salts is selected from NaCl, KCl, NaH$_2$PO$_4$, NaHCO$_3$, CaCl$_2$, and MgCl$_2$ and combinations thereof. In some embodiments, the amount of salt in the supplement has a concentration of 0.5-5 g/L upon hydration to form a cell culture medium. In one embodiment, the salt of the cell culture media supplement is magnesium chloride. In some embodiments, the magnesium chloride of the supplement has a concentration of about 1.428 g/L upon hydration to form a cell culture medium.

The one or more growth factors of the cell culture media supplement are not limiting. In some embodiments, the growth factor is Amphiregulin, Angiopoietin, Betacellulin, (Bone Morphogenic protein-13, Bone Morphogenic protein-14, Bone Morphogenic protein-2, Human BMP-3, Bone Morphogenic protein-4, Human BMP-5, Bone Morphogenic protein-6, Bone Morphogenic protein-7, Human CD135 Ligand/Flt-3 Ligand, Human Granulocyte Colony Stimulating Factor (G-CSF), Human Granulocyte Macrophage Colony Stimulating Factor (GM-CSF), Human Macrophage Colony Stimulating Factor (M-CSF), Human Cripto-1, Human CTGF (Connective tissue growth factor), Human EGF (Epidermal Growth Factor), Human EG-VEGF (Endocrine-Gland-Derived Vascular Endothelial Growth Factor), Human Erythropoietin (EPO), Human FGF (Fibroblast Growth Factors 1-23), Human GDF-11, Human GDF-15, Human GDF-8, Human Growth Hormone Releasing Factor (GHRF, GRF, GHRH, Growth Hormone Releasing Hormone), Human Heparin Binding Epidermal Growth Factor (HB-EGF), Human Hepatocyte Growth Factor (HGF), Human Heregulin beta 1, Human insulin, Human IGF-1 (Insulin-like Growth Factor-1), Human IGF-2 (Insulin-like Growth Factor-2), Human IGFBP-1 (Insulin-like Growth Factor Binding Protein 1), Human IGFBP-3 (Insulin-like Growth Factor Binding Protein 3), intestinal trefoil factor (ITF), Human keratinocyte growth factors 1 & 2, Human Leukemia Inhibitory Factor (LIF), Human MSP, Human Myostatin, Human Myostatin, pro (propeptide), Human NRG1, Human NGF, Human Oncostatin M, Human Osteoblast Specific Factor 1 (OSF-1, Pleiotrophin), Human PD-ECGF (Platelet-derived endothelial cell growth factor), Human PDGF, Human PlGF, Human Placental Growth Factor 1 (PLGF1), Human Placental Growth Factor 2 (PLGF2), Human SCGF-a (Stem Cell Growth Factor-alpha), Human SCGF-b (Stem Cell Growth Factor-beta), Human Stem Cell Factor (SCF)/CD117 Ligand, Human Thrombopoietin (TPO, THPO), Human Transforming Growth Factor, Human TGF-alpha (Transforming Growth Factor-alpha, TGFa), Human TGF-beta 1 (Transforming Growth Factor-beta1, TGFb), Human TGF-beta 1.2 (Transforming Growth Factor-beta1, TGFb), Human TGF-beta 2 (Transforming Growth Factor-beta2, TGFb), Human TGF-beta 3 (Transforming Growth Factor-beta3, TGFb), Human VEGF (Vascular Endothelial Growth Factor), Human VEGF-121, Human VEGF-165, and Human VEGF-A. The above list would include sequence variants, analogues and agonists, including amino acid substitutions and/or extensions and/or deletions of the aforementioned factors (for example, IGF-I would include LR3-IGF-I, U.S. Pat. No. 5,330,971) both naturally occurring and synthetic.

In some embodiments, the growth factor comprises insulin. Insulin can be recombinantly produced, isolated from natural sources, or synthetic. In some embodiments, the insulin is human recombinant insulin (EMD MILLIPORE CORPORATION). In some embodiments, insulin has a concentration of 0.5-15 mg/L upon hydration to form a cell culture medium. In some embodiments, the insulin has a concentration of about 3 mg/L upon hydration to form a cell culture medium.

In some embodiments, the one or more inorganic ions of the cell culture media supplement comprises trace metals selected from ammonium molybdate, chromium potassium sulfate, cupric sulfate, lithium chloride, manganese sulfate, sodium metasilicate, ammonium paramolybdate, ammonium vanadium oxide, ferrous sulfate, nickel chloride, selenious acid, stannous chloride, zinc sulfate, and combinations thereof. In some embodiments, the ammonium molybdate is ammonium molybdate 4H$_2$O; the chromium potassium sulfate is chromium potassium sulfate 12H$_2$O, the cupric sulfate is cupric sulfate 5H$_2$O, the lithium chloride is lithium chloride (anhydrous), the manganese sulfate is manganese sulfate H$_2$O and the sodium metasilicate is sodium metasilicate 9H2O. The chemicals are generally available from Sigma Aldrich and VWR.

In some embodiments, the one or more inorganic ions of the cell culture media supplement has the following final concentration upon hydration to form a cell culture medium:
i) 0.0005-0.01 mg/L of ammonium molybdate 4H$_2$O;
ii) 0.0001-0.01 mg/L of chromium potassium sulfate 12H$_2$O;
iii) 0.001-0.125 mg/L of cupric sulfate 5H$_2$O;
iv) 0.001-0.1 mg/L of lithium chloride (anhydrous);
v) 0.00004-0.004 mg/L of manganese sulfate H$_2$O; and
vi) 0.04-4.2 mg/L of sodium metasilicate 9H2O.

In some embodiments, the one or more inorganic ions of the cell culture media supplement comprises a combination of ammonium molybdate 4H$_2$O, chromium potassium sulfate 12H$_2$O, cupric sulfate 5H$_2$O, lithium chloride (anhydrous), manganese sulfate H$_2$O, and sodium metasilicate 9H2O. In some embodiments, the trace metals provide the following final concentration upon hydration to form a cell culture medium:
  i) about 0.0037 mg/L of ammonium molybdate 4H$_2$O;
  ii) about 0.001 mg/L of chromium potassium sulfate 12H$_2$O;
  iii) about 0.0125 mg/L of cupric sulfate 5H$_2$O;
  iv) about 0.01 mg/L of lithium chloride (anhydrous);
  v) about 0.000452 mg/L of manganese sulfate H$_2$O; and
  vi) about 0.4263 mg/L of sodium metasilicate 9H2O.

The amino acid supplement of the cell culture media supplement can include any amino acid, including glycine, alanine, valine, leucine, isoleucine, arginine, lysine, aspartic acid, cysteine, cysteine, methionine, phenylalanine, proline, threonine, tryptophan, tyrosine, asparagine, glutamine, histidine, and serine. In some embodiments, the amino acid supplement of the cell culture media supplement comprises a combination of asparagine, glutamine, histidine, and serine. Amino acids suitable for cell culture are generally available from Kyowa Hakko U.S.A., Research Organics, Inc. and Ajinomoto AminoScience LLC. In some embodiments, the amino acid supplement has the following final concentration upon hydration to form a cell culture medium:
  i) 0.007-0.07 g/L asparagine H$_2$O;
  ii) 0.25-2.5 g/L glutamine;
  iii) 0.5-5.0 g/L histidine, free base; and
  iv) 0.01-0.1 g/L serine.

In some embodiments, the amino acid supplement has the following final concentration upon hydration to form a cell culture medium:
  i) about 0.0225 g/L asparagine H$_2$O;
  ii) about 0.73 g/L glutamine;
  iii) about 1.552 g/L histidine; and
  iv) about 0.03676 g/L serine.

The buffer of the cell culture media supplement is not limiting. A "buffer" is a solution that resists changes in pH by the action of its acid-base conjugate components. Various buffers which can be employed depending, for example, on the desired pH of the buffer (and on the cells growth and metabolic properties, cell culture cultivation system, pH control and medium used) are described in Buffers. *A Guide for the Preparation and Use of Buffers in Biological Systems*, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these. In some embodiments, the buffer is selected from the group consisting of 3-(N-morpholino)propanesulfonic acid (MOPS) free acid, 3-(N-morpholino)propanesulfonic acid (MOPS) Na, hydroxyethyl piperazineethanesulfonic acid (HEPES) and sodium bicarbonate. In some embodiments, the formulation comprises a combination of MOPS free acid and MOPS Na. In some embodiments, the buffers of the cell culture media supplement provide the following final concentration when the compounded cell culture medium powder formulation is combined with water to form a cell culture medium:
  i) 0.3-3 g/L MOPS free acid; and
  ii) 1.0-10 g/L MOPS Na.

The anti-foaming agent of the invention is not limiting. In some embodiments, the anti-foaming agent of the compounded cell culture medium powder formulation comprises an ionic or non-ionic surfactant. Anti-foaming (also called 'defoaming') agents can include oil, water, silicone, polyethylene glycol/copolymers, and alkyl polyacrylates-based. Common examples include: Schill and Schelinger's Struktol SB2121 (a polyalkylene glycol), Schill and Schelinger's Struktol J673A (an alkoxylated fatty acid ester on a vegetable base), Fluka P2000 (a polypropylene glycol), Sigma Antifoam A (a 30% emulsion of silicone polymer) and Sigma Antifoam C (a 30% emulsion of silicone polymer) (Ref: Sarah J Routledge (2012); Beyond de-foaming: the effects of antifoams on bioprocess productivity. Computational and Structural Biotechnology Journal. 3(4) and references within). In some embodiments, the antifoaming agent is a polyol copolymer based on ethylene oxide and propylene oxide.

In some embodiments, the anti-foaming agent is Pluronic F68. Pluronic F-68 is a nonionic block copolymer with an average molecular weight of 8400, consisting of a center block of poly(oxypropylene) (20% by weight) and blocks of poly(oxyethylene) at both ends. In some embodiments, other polyols can also be used and include nonionic block copolymers of poly(oxyethylene) and poly(oxypropylene) having molecular weights ranging from about 1000 to about 16,000.

In some embodiments, the anti-foaming agent is Pluronic F68 and has a concentration of 0.1-10 g/L when the compounded cell culture medium powder formulation is combined with water to form a cell culture medium. In some embodiments, the Pluronic F68 has a concentration of about 1 g/L when the compounded cell culture medium powder formulation is combined with water to form a cell culture medium.

In some embodiments, the compounded cell culture medium powder formulation comprises the following components which provide the following final concentration upon hydration to form a cell culture medium:
  i) 0.0003-0.003 g/L biotin;
  ii) 0.035-0.33 g/L calcium chloride;
  iii) 0.003-0.03 g/L choline chloride;
  iv) 0.0002-0.002 g/L cyanocobalamin (B12);
  v) 1-10 g/L D+ mannose;
  vi) 0.001-0.01 g/L D-calcium pantothenate;
  vii) 0.3-3.0 g/L dextrose (anhydrous);
  viii) 0.00003-0.0003 g/L DL-alpha-lipoic acid;
  ix) 0.00002-0.00015 g/L ferric nitrate 9H$_2$O;
  x) 0.0001-0.0015 g/L ferrous sulfate 7H$_2$O;
  xi) 0.001-0.01 g/L folic acid;
  xii) 0.007-0.20 g/L glycine;
  xiii) 0.001-0.01 g/L hypoxanthine 2Na;
  xiv) 0.005-0.05 g/L I-inositol;
  xv) 0.003-0.03 g/L L-alanine;
  xvi) 0.08-1.4 g/L L-arginine;
  xvii) 0.006-0.16 g/L L-asparagine;
  xviii) 0.005-0.10 g/L L-aspartic acid;
  xix) 0.005-0.05 g/L L-cysteine HCl H$_2$O;
  xx) 0.02-0.2 g/L L-cystine 2HCl;
  xxi) 0.005-0.15 g/L L-glutamic acid (anhydrous);
  xxii) 0.02-0.6 g/L L-glutamine;
  xxiii) 0.0003-0.003 g/L L-glutathione;
  xxiv) 0.02-0.2 g/L L-histidine HCl;
  xxv) 0.03-0.9 g/L L-isoleucine;
  xxvi) 0.03-0.9 g/L L-leucine;
  xxvii) 0.05-1.5 g/L L-lysine;
  xxviii) 0.01-0.3 g/L L-methionine;
  xxix) 0.02-0.6 g/L L-phenylaline;
  xxx) 0.008-0.25 g/L L-proline;
  xxxi) 0.009-0.25 g/L L-serine;
  xxxii) 0.03-0.9 g/L L-threonine;
  xxxiii) 0.006-0.16 g/L L-tryptophan;
  xxxiv) 0.03-0.9 g/L L-tyrosine 2Na 2H$_2$O;

xxxv) 0.03-0.9 g/L L-valine;
xxxvi) 0.01-0.18 g/L magnesium chloride
xxxvii) 0.02-0.12 g/L magnesium sulfate anhydrous;
xxxviii) 0.001-0.01 g/L niacinamide;
xxxix) 0.0005-0.005 g/L O-phoshphoryl-ethanolamine;
xl) 0.1-1.0 g/L potassium chloride;
xli) 0.00002-0.0002 g/L putrescine 2HCl;
xlii) 0.001-0.01 g/L pyridoxal HCl;
xliii) 0.00001-0.0001 g/L pyridoxine HCl,
xliv) 0.0001-0.001 g/L riboflavin,
xlv) 2.0-15 g/L sodium chloride,
xlvi) 0.02-0.2 g/L sodium phosphate monobasic $H_2O$,
xlvii) 0.02-0.2 g/L sodium phosphate dibasic anhydrous,
xlviii) 0.015-0.15 g/L sodium pyruvate,
xlix) 0.001-0.01 g/L thiamine HCl,
l) 0.0001-0.001 g/L thymidine,
li) 0.00015-0.0015 g/L zinc sulfate $7H_2O$,
lii) 0.0000006-0.000006 g/L cupric sulfate $5H_2$,
liii) 0.0000005-0.000008 g/L selenium dioxide,
liv) 0.00001-0.0001 g/L linoleic acid,
lv) 0.0001-0.001 g/L beta-mercaptoethanol;
lvi) 0.0003-0.005 g/L ethanolamine FB;
lvii) 0.5-5 g/L MgCl2;
lviii) 0.5-15 mg/L insulin;
lix) 0.0005-0.01 mg/L of ammonium molybdate $4H_2O$;
lx) 0.0001-0.01 mg/L of chromium potassium sulfate $12H_2O$;
lxi) 0.001-0.125 mg/L of cupric sulfate $5H_2O$;
lxii) 0.001-0.1 mg/L of lithium chloride (anhydrous);
lxiii) 0.00004-0.004 mg/L of manganese sulfate $H_2O$;
lxiv) 0.04-4.2 mg/L of sodium metasilicate 9H2O;
lxv) 0.007-0.07 g/L asparagine $H_2O$;
lxvi) 0.25-2.5 g/L glutamine;
lxvii) 0.5-5.0 g/L histidine, free base;
lxviii) 0.01-0.1 g/L serine;
lxix) 0.3-3 g/L MOPS free acid;
lxx) 1.0-10 g/L MOPS Na; and
lxxi) 0.1-10 g/L Pluronic F68.

In another embodiment, the invention provides a method of making the compounded cell culture medium powder formulation of the invention, comprising combining the components of the basal medium powder; one or more salts; one or more growth factors; one or more inorganic ions; an amino acid supplement comprising one or more of asparagine, glutamine, histidine, and serine; one or more buffers; and one or more anti-foaming agents. The order of addition of the components of the compounded cell culture medium powder formulation is not limiting. In one embodiment, each component of the composition is added individually to make the compounded cell culture medium powder formulation. In some embodiments, the basal media is first made as a batch and then is combined with the other components that make up the culture media supplement. In some embodiments, the cell culture media supplement can be made as a batch, and later combined with a batched basal media powder or combined with the components of the basal media powder by a sequential addition to make the compounded cell culture medium powder formulation.

A cell culture medium can be prepared using the compounded cell culture medium powder formulation of the invention by performing a hydration step. In another aspect, the invention provides a method of making a cell culture medium for growing cells, comprising contacting the compounded cell culture medium powder formulation with water, thereby making a cell culture medium for growing cells. In one embodiment, the cells are mammalian cells. In some embodiments, the components are substantially dissolved in the water. In some embodiments, a tank is filled with water and the compounded cell culture medium powder formulation is added to the tank. The user can optionally perform quality control process steps to make sure that the powder is dissolved, by mixing, and testing osmolality, conductivity, and the pH to ensure all of the components are present in the targeted amounts.

In one embodiment, the invention provides a method of making a cell culture medium for growing cells, comprising substantially dissolving the compounded cell culture medium powder formulation with water, and optionally further comprising combining a solution comprising $FeSO_4$ $7H_2O$ and a chelating agent. In some embodiments, the water and solution comprising $FeSO_4$ $7H_2O$ and a chelating agent are mixed first, followed by addition of the compounded cell culture medium powder formulation. In some embodiments, the chelating agent is ethylenediaminetetraacetic acid (EDTA). In some embodiments, the $FeSO_4$ $7H_2O$ and EDTA have the following final concentration in the cell culture medium: 0.004-0.04 g/L $FeSO_4$ $7H_2O$; and 0.006-0.06 g/L EDTA. In some embodiments, the $FeSO_4$ $7H_2O$ and EDTA have the following final concentration in the cell culture medium: about 0.0138 g/L $FeSO_4$ $7H_2O$ and about 0.018625 g/L EDTA.

In another embodiment, the invention provides a method of culturing cells, comprising, comprising contacting cells with a cell culture medium of the invention and culturing the cells in the medium for a period of time. In some embodiments, the cells are incubated in fed-batch or semi-batch culture. In some embodiments, the cells are incubated in a perfusion culture.

In some embodiments, the cell culture medium is for expressing a protein of interest. In another embodiment, the invention provides a method of producing a protein of interest, comprising contacting cells expressing the protein of interest with a cell culture medium; culturing the cells in the medium for a period of time; and isolating the protein of interest from the cell culture medium.

In some embodiments the protein of interest is selected from the group consisting of coagulation Factor VIII (FVIII), and functional variants and fragments thereof. In some embodiments, the FVIII polypeptides include allelic variations, glycosylated versions, modifications and fragments resulting in derivatives of FVIII so long as they contain the functional segment of human FVIII and the essential, characteristic human FVIII functional activity.

In some embodiments, the FVIII molecules useful for expression using the compounded media of the present invention include the full length protein, precursors of the protein, subunits or fragments of the protein, and variants and antigenic fragments thereof. Reference to FVIII is meant to include all potential forms of such proteins.

Examples of recombinant FVIII include Recombinate™ and Advate®, both manufactured and sold by Baxter Healthcare Corporation; ReFacto®, a B-domain deleted form of FVIII manufactured and sold by Wyeth Corporation; and KOGENATE, manufactured and sold by Bayer Corporation. In some embodiments, the FVIII polypeptides to be expressed comprise full-length human FVIII. In some embodiments, the full length FVIII comprises an amino acid sequence selected from the group consisting of SEQ ID NO: 1, SEQ ID NO: 2 and a combination thereof, although allelic variants are possible. As a secreted protein, FVIII contains a signal sequence that is proteolytically cleaved during the translation process. Following removal of the 19 amino acid signal sequence, the first amino acid of the secreted FVIII product is an alanine.

In some embodiments, the human FVIII is B-domain deleted FVIII (BDD). As used herein, BDD is characterized by having the amino acid sequence which contains a deletion of all but 14 amino acids of the B-domain of FVIII. The first 4 amino acids of the B-domain (SEQ ID NO:3) are linked to the 10 last residues of the B-domain (NPPVLKRHQR, SEQ ID NO:4). In some embodiments, the BDD FVIII comprises an amino acid sequence selected from the group consisting of SEQ ID NO: 5 and SEQ ID NO: 6 and a combination thereof.

In some embodiments, FVIII can be modified with a biocompatible polymer, such as PEG. Pegylated forms of Factor VIII are disclosed in WO 2006/053299 and U.S. Patent Application Pub. No. 20060115876, which are incorporated by reference herein.

In the examples of FVIII that follow, the FVIII muteins are named in a manner conventional in the art. As used herein, a "mutein" is a genetically engineered protein arising as a result of a laboratory induced mutation to a protein or polypeptide The convention for naming mutants is based on the amino acid sequence for the mature, full length Factor VIII as provided in SEQ ID NO:2.

As is conventional and used herein, when referring to mutated amino acids in BDD FVIII, the mutated amino acid is designated by its position in the sequence of full-length FVIII. For example, a particular mutein is designated K1808C because it changes the lysine (K) at the position analogous to 1808 in the full-length sequence to cysteine (C). In some embodiments, for the mutants discussed below, a cysteine replaces the natural amino acid at the designated location of the full length FVIII or the B-domain deleted FVIII, and a biocompatible polymer, such as PEG, is attached to the cysteine residue.

The predefined site for covalent binding of a biocompatible polymer, such as PEG, is best selected from sites exposed on the surface of the polypeptide that are not involved in FVIII activity or involved in other mechanisms that stabilize FVIII in vivo, such as binding to vWF. Such sites are also best selected from those sites known to be involved in mechanisms by which FVIII is deactivated or cleared from circulation. Selection of these sites is discussed in detail below. Preferred sites include an amino acid residue in or near a binding site for (a) low density lipoprotein receptor related protein, (b) a heparin sulphate proteoglycan, (c) low density lipoprotein receptor and/or (d) factor VIII inhibitory antibodies. By "in or near a binding site" means a residue that is sufficiently close to a binding site such that covalent attachment of a biocompatible polymer to the site would result in steric hindrance of the binding site. Such a site is expected to be within 20 Angstroms of a binding site, for example.

In one embodiment, the biocompatible polymer is covalently attached to the functional factor VIII polypeptide at an amino acid residue in or near (a) a factor VIII clearance receptor, (b) a binding site for a protease capable of degradation of factor VIII and/or (c) a binding site for factor VIII inhibitory antibodies. The protease may be activated protein C (APC). In another embodiment, the biocompatible polymer is covalently attached at the predefined site on the functional factor VIII polypeptide such that binding of low-density lipoprotein receptor related protein to the polypeptide is less than to the polypeptide when it is not conjugated, and preferably more than twofold less. In one embodiment, the biocompatible polymer is covalently attached at the predefined site on the functional factor VIII polypeptide such that binding of heparin sulphate proteoglycans to the polypeptide is less than to the polypeptide when it is not conjugated, and preferably is more than twofold less. In a further embodiment, the biocompatible polymer is covalently attached at the predefined site on the functional factor VIII polypeptide such that binding of factor VIII inhibitory antibodies to the polypeptide is less than to the polypeptide when it is not conjugated, preferably more than twofold less than the binding to the polypeptide when it is not conjugated. In another embodiment, the biocompatible polymer is covalently attached at the predefined site on the functional factor VIII polypeptide such that binding of low density lipoprotein receptor to the polypeptide is less than to the polypeptide when it is not conjugated, preferably more than twofold less. In another embodiment, the biocompatible polymer is covalently attached at the predefined site on the functional factor VIII polypeptide such that a plasma protease degrades the polypeptide less than when the polypeptide is not conjugated. In a further embodiment, the degradation of the polypeptide by the plasma protease is more than twofold less than the degradation of the polypeptide when it is not conjugated as measured under the same conditions over the same time period.

LRP, LDL receptor, or HSPG binding affinity for FVIII can be determined using surface plasmon resonance technology (Biacore). For example, FVIII can be coated directly or indirectly through a FVIII antibody to a Biacore chip, and varying concentrations of LRP can be passed over the chip to measure both on-rate and off-rate of the interaction (Bovenschen N. et al., 2003, *J. Biol. Chem.* 278(11), pp. 9370-7). The ratio of the two rates gives a measure of affinity. A two-fold, preferably five-fold, more preferably ten-fold, and even more preferably 30-fold decrease in affinity upon PEGylation would be desired.

Degradation of a FVIII by the protease APC can be measured by any of the methods known to those of skill in the art.

In one embodiment, the biocompatible polymer is covalently attached to the polypeptide at one or more of the FVIII (SEQ ID NO:2) amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284. In another embodiment, the biocompatible polymer is covalently attached to the polypeptide at one or more of factor VIII (SEQ ID NO:2) amino acid positions 377, 378, 468, 491, 504, 556, 1795, 1796, 1803, 1804, 1808, 1810, 1864, 1903, 1911 and 2284 and (1) the binding of the conjugate to low-density lipoprotein receptor related protein is less than the binding of the unconjugated polypeptide to the low-density lipoprotein receptor related protein; (2) the binding of the conjugate to low-density lipoprotein receptor is less than the binding of the unconjugated polypeptide to the low-density lipoprotein receptor; or (3) the binding of the conjugate to both low-density lipoprotein receptor related protein and low-density lipoprotein receptor is less than the binding of the unconjugated polypeptide to the low-density lipoprotein receptor related protein and the low-density lipoprotein receptor. In one embodiment, residue 1804 in a B-domain deleted FVIII is mutated to cysteine and conjugated to PEG.

In a further embodiment, the biocompatible polymer is covalently attached to the polypeptide at one or more of FVIII (SEQ ID NO:2) amino acid positions 377, 378, 468, 491, 504, 556 and 711 and the binding of the conjugate to heparin sulphate proteoglycan is less than the binding of the unconjugated polypeptide to heparin sulphate proteoglycan. In a further embodiment, the biocompatible polymer is covalently attached to the polypeptide at one or more of the factor VIII (SEQ ID NO:2) amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284 and the conjugate has less binding to factor VIII inhibitory antibodies than the unconjugated polypeptide. In a further embodiment, the biocompatible polymer is covalently attached to the polypeptide at one or more of the factor VIII (SEQ ID NO:2) amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284, and preferably at one or more of positions 377, 378, 468, 491, 504, 556, and 711 and the conjugate has less degradation from a plasma protease capable of factor VIII degradation than does the unconjugated polypeptide. More preferred, the plasma protease is activated protein C.

In a further embodiment, the biocompatible polymer is covalently attached to B-domain deleted factor VIII at amino acid position 129, 491, 1804, and/or 1808, more preferably at 491 or 1808. In a further embodiment, the biocompatible polymer is attached to the polypeptide at factor VIII amino acid position 1804 and comprises polyethylene glycol. Preferably, the one or more predefined sites for biocompatible polymer attachment are controlled by site specific cysteine mutation.

One or more sites, preferably one or two, on the functional factor VIII polypeptide may be the predefined sites for polymer attachment. In particular embodiments, the polypeptide is mono-PEGylated or diPEGylated.

The invention also relates to a method for the preparation of the conjugate comprising mutating a nucleotide sequence that encodes for the functional factor VIII polypeptide to substitute a coding sequence for a cysteine residue at a pre-defined site; expressing the mutated nucleotide sequence to produce a cysteine enhanced mutein; purifying the mutein; reacting the mutein with the biocompatible polymer that has been activated to react with polypeptides at substantially only reduced cysteine residues such that the conjugate is formed; and purifying the conjugate. In another embodiment, the invention provides a method for site-directed PEGylation of a factor VIII mutein comprising: (a) expressing a site-directed factor VIII mutein wherein the mutein has a cysteine replacement for an amino acid residue on the exposed surface of the factor VIII mutein and that cysteine is capped; (b) contacting the cysteine mutein with a reductant under conditions to mildly reduce the cysteine mutein and to release the cap; (c) removing the cap and the reductant from the cysteine mutein; and (d) at least about 5 minutes, and preferably at least 15 minutes, still more preferably at least 30 minutes after the removal of the reductant, treating the cysteine mutein with PEG comprising a sulfhydryl coupling moiety under conditions such that PEGylated factor VIII mutein is produced. The sulfhydryl coupling moiety of the PEG is selected from the group consisting of thiol, triflate, tresylate, aziridine, oxirane, S-pyridyl and maleimide moieties, preferably maleimide.

In one embodiment, one or more surface BDD amino acids is replaced with a cysteine, producing the cysteine mutein in a mammalian expression system, reducing a cysteine which has been capped during expression by cysteine from growth media, removing the reductant to allow BDD disulfides to reform, and reacting with a cysteine-specific biocompatible polymer reagent, such as such as PEG-maleimide. Examples of such reagents are PEG-maleimide with PEG sizes such as 5, 22, or 43 kD available from Nektar Therapeutics of San Carlos, Calif. under Nektar catalog numbers 2D2MOH01 mPEG-MAL MW 5,000 Da, 2D2MOP01 mPEG-MAL MW 20 kD, 2D3X0P01 mPEG2-MAL MW 40 kD, respectively, or 12 or 33 kD available from NOF Corporation, Tokyo, Japan under NOF catalog number Sunbright ME-120MA and Sunbright ME-300MA, respectively. The PEGylated product is purified using ion-exchange chromatography to remove unreacted PEG and using size-exclusion chromatography to remove unreacted BDD. This method can be used to identify and selectively shield any unfavorable interactions with FVIII such as receptor-mediated clearance, inhibitory antibody binding, and degradation by proteolytic enzymes. We noted that the PEG reagent supplied by Nektar or NOF as 5 kD tested as 6 kD in our laboratory, and similarly the PEG reagent supplied as linear 20 kD tested as 22 kD, that supplied as 40 kD tested as 43 kD and that supplied as 60 kD tested as 64 kD in our laboratory. To avoid confusion, we use the molecular weight as tested in our laboratory in the discussion herein, except for the 5 kD PEG, which we report as 5 kD as the manufacturer identified it.

In addition to cysteine mutations at positions 491 and 1808 of BDD (disclosed above), positions 487, 496, 504, 468, 1810, 1812, 1813, 1815, 1795, 1796, 1803, and 1804 were mutated to cysteine to potentially allow blockage of LRP binding upon PEGylation. Also, positions 377, 378, and 556 were mutated to cysteine to allow blockage of both LRP and HSPG binding upon PEGylation. Positions 81, 129, 422, 523, 570, 1864, 1911, 2091, and 2284 were selected to be equally spaced on BDD so that site-directed PEGylation with large PEGs (>40 kD) at these positions together with PEGylation at the native glycosylation sites (41, 239, and 2118) and LRP binding sites should completely cover the surface of BDD and identify novel clearance mechanism for BDD.

In one embodiment, the cell culture medium contains cysteines that "cap" the cysteine residues on the mutein by forming disulfide bonds. In the preparation of the conjugate, the cysteine mutein produced in the recombinant system is capped with a cysteine from the medium and this cap is removed by mild reduction that releases the cap before adding the cysteine-specific polymer reagent. Other methods known in the art for site-specific mutation of FVIII may also be used, as would be apparent to one of skill in the art.

In some embodiments, the FVIII is selected from wild-type FVIII, B-domain deleted FVIII and FVIII conjugated with a biocompatible polymer. In some embodiments, the biocompatible polymer is polyethylene glycol (PEG). In some embodiments, the PEG is covalently attached to the polypeptide at one or more of the factor VIII amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLE 1

The current method of media preparation for producing Factor VIII involves the addition of several add-back solutions and dry powder components/mixes in order to construct their cell culture medium. Several related powder variations were evaluated that included some or all of the add-backs (milled into the DPM) in order to identify a more complex (i.e., fewer add-backs) powder formulation that has acceptable growth and performance characteristics. The goal is to streamline medium formulation process and reduce the supply chain complexity (as seen in Table 1).

For producing a powdered media formulation suitable for producing a pegylated Factor VIII, an optimized FVIII powder formulation was blended with an amino acid powder blend (3×AA mix) into one formulation and the characteristics were evaluated.

Materials/Methods

Materials

The balance was a Sartorius MSA124S; the osmometer was Advanced Instruments, Model 3300; the pH readings were taken with a ThermoOrion Model 720A; turbidity readings measured on a Hach 2100N Turbidimeter; Insulin UPLC analysis was done via Acquity H-Class, Acquity BE-1H300 C4 column; Insulin ELISA quantitation was done using a Millipore ELISA kit; Amino acid quantitation was done via Waters HPLC, Zorbax Eclipse AAA column; the ICP analyses were done on an Agilent 720-ES ICP-OES.

Methods

The DPM versions and all associated add-back solutions and powders were manufactured by SAFC's Immediate Advantage department. The add-back powders and solutions are summarized in Table 1. The versions, description of the powders, and SAFC product numbers are summarized in Table 2.

TABLE 1

Current Media Formulation Materials

| Description | Conc. In 1 L |
|---|---|
| R3* w/o Phenol Red | 13.036 g/L |
| rH-Insulin | 3.0 mg/L |
| | (0.6 mL/L) |
| MgCl2 Anhydrous* | 1.428 g/L |
| 10 mM FeSO4/EDTA Soln. (TE #1) | 5 mL/L |
| FeSO4 7H2O | 0.0138 g/L |
| EDTA 2Na 2 H2O | 0.018625 g/L |
| Trace Metal Solution #2 | 0.1 mL/L |
| Ammonium Molybdate 4H2O | 0.0037 mg/L |
| Chromium Potassium Sulfate 12H2O | 0.001 mg/L |
| Cupric Sulfate 5H2O | 0.0125 mg/L |
| Lithium Chloride Anhydrous | 0.01 mg/L |
| Manganese Sulfate H2O | 0.000452 mg/L |
| Sodium Metasilicate 9H2O | 0.4263 mg/L |
| Factor VIII (non-pegylated) Supplement | 7.856 g/L |
| Asparagine H2O | 0.0225 g/L |
| Glutamine | 0.73 g/L |
| Histidine | 1.552 g/L |
| Serine | 0.03676 g/L |
| Lutrol (Pluronic F68) | 1.0 g/L |
| MOPS Free Acid | 1.0465 g/L |
| MOPS Na | 3.468 g/L |
| 3x AA Mix (for pegylated FVIII only) | 2.594 g/L |

*See the formulation of Example 2, below.

TABLE 2

Various Factor VIII (non-pegylated) formulations evaluated

| Version | Description |
|---|---|
| 1 | Base Media (control) - R3 without Phenol Red (68213C) |
| 2 | Base Media + All Additions |
| 2.1 | Base Media + All Additions; adjusted histidine HCl and FB |
| 3 | Base Media + All Additions except TE Solution #1 |
| 3.1 | Base Media + All Additions except TE Solution #1; adjusted histidine HCl |
| 3.2 | Base Media + All Additions except TE Solution #1; adjusted histidine FB |
| 3.3 | Base Media + All Additions except TE Solution #1; adjusted histidine HCl and FB |
| 4 | Base Media + All Additions except amino acids mix |
| 5 | Base Media + All Additions except TE Solution #1 and amino acid mix |
| 6 | Base Media + All Additions except Lutrol and MOPS |

The pegylated FVIII formulation was a combination of 22.29 g/L non-pegylated FVIII Version 3.3 mixed with 2.594 g/L 3x AA Production Mix.

Results

These versions were tested for the following characteristics:
1) pH and osmolality of the hydrated powder
2) Analysis of amino acid concentration
3) Analysis of Fe concentration
4) Analysis of insulin concentration Tables 3A and 3B summarize the data for the non-pegylated FVIII versions tested.

TABLE 3A

Finished product results for non-pegylated FVIII Versions 1-6

| | Hydration | | Amino Acid Data (Percent of control (Ver. 1); %) | | | |
|---|---|---|---|---|---|---|
| Version | pH | Osmolality | Ser | Asn | Gln | His |
| 1 | 7.49 | 346 | NA | NA | NA | NA |
| 2 | 6.93 | 333 | 97.7 | 98.0 | 96.8 | 72.2 |
| 2.1 | 7.44 | 339 | 102.8 | 97.2 | 102.7 | 101.8 |
| 3 | 6.96 | 334 | 101.2 | 97.8 | 96.8 | 71.6 |
| 3.1 | 7.12 | NA | NA | NA | NA | 111.4 |
| 3.2 | 8.03 | NA | NA | NA | NA | 113.4 |
| 3.3 | 7.56 | 329 | 103.5 | 98.6 | 100.8 | 100.2 |
| 4 | 6.15 | 282 | 47.4 | 46.6 | 48.4 | 3.5 |
| 5 | 6.24 | 285 | 46.7 | 48.1 | 48.0 | 3.4 |
| 6 | 5.09 | 305 | 97.8 | 97.4 | 96.8 | 72.3 |

TABLE 3B

Finished product results for non-pegylated FVIII Versions 1-6

| | | Insulin | |
|---|---|---|---|
| Version | ICP Data Fe (ppm) | HPLC (mg/L) | ELISA (retests if applicable) (mg/L) |
| Theoretical | 4.0 | 3.00 | 3.00 |
| 1 | 4.1 | 3.60 | 1.26, 2.62 |
| 2 | 2.9 | 3.05 | |
| 2.1 | 2.8 | 3.40 | 1.4 |
| 3 | 0.4 | 3.04 | |
| 3.1 | NA | | |
| 3.2 | NA | | |
| 3.3 | 0.33 | 3.95 | 0.880, 1.26, 3.70 |
| 4 | 2.9 | | |
| 5 | 0.4 | | |
| 6 | 3.0 | | |

The use of HPLC for insulin quantitation is more accurate and precise than using the Millipore ELISA kit for insulin. The HPLC method is extremely similar to the USP HPLC method for insulin quantitation, and thus is robust and rugged, and its accuracy and precision have been established. In contrast, the ELISA method is designed for simple insulin formulations, and is not likely optimized for use in such complex formulations found in cell culture. It is likely the inconsistent results seen with the ELISA test is due to component interference with insulin binding (or competitive inhibition), therefore making the ELISA test sub-optimal for accurate quantitation of insulin in such complex cell culture media.

Table 4 outlines the iron residue left on the 0.22 μm filter paper used to filter 1 L of Version 1, Version 2.1, and Version 3.3. The result of this iron testing was the basis for selecting the Version 3.3 as the formulation for use.

TABLE 4

Iron amounts from rinsed 0.22 μm filter papers used to individually filter various versions of non-pegylated FVIII

| Trace Element | Control Blank Filter Paper (μg) | Version 2.1 Prep A (μg) | Version 2.1 Prep B (μg) | Version 3.3 Prep A (μg) | Version 3.3 Prep B (μg) | Version 1 Prep A (μg) | Version 1 Prep B (μg) |
|---|---|---|---|---|---|---|---|
| Fe | >10 | 190 | 170 | 1 | 1 | 2 | 1 |

Table 5 summarizes the data for the KG-N version tested.

TABLE 5

Finished product results for pegylated FVIII version

| Lot # | pH | Hydration Osmolality | Amino Acid Data (Percent of control; %) | | | |
|---|---|---|---|---|---|---|
| | | | Ser | Asn | Gln | His |
| 13D530 | 7.57 | 354 | 99.7 | 97.4 | 96.4 | 98.9 |

| Lot # | ICP Data Fe (ppm) | Insulin HPLC (mg/L) | Insulin ELISA (retests if applicable) (mg/L) |
|---|---|---|---|
| 13D530 | 0.33 | 3.62 | 0.890, 1.09 |

Conclusions

The final version of the non-pegylated FVIII was Version 3.3. This is the complete media minus the majority (97.1%) of iron and all of the EDTA in the formulation. This iron/EDTA-free dry powder formulation (utilizing an iron/EDTA liquid add-back) was selected as the formulation due to the discovery that Version 2.1 (containing iron and EDTA milled into the DPM) did not properly chelate (i.e., solubilize) the iron upon hydration, and thus the iron was being filtered out of the solution (Table 4).

The analytical evaluation of Version 3.3 measured insulin concentration, amino acid concentrations, and pH (upon hydration) that was not significantly different than a fully formulated Version 1 (the control).

The pegylated FVIII formulation is the non-pegylated FVIII formulation fortified with additional amino acids.

EXAMPLE 2

This example shows an exemplary basal medium which can be enhanced by further compounding into the compounded media formulation of the invention. In this example, an indicator such as phenol red, is included, however, the indicator can be omitted.

| Component | Units/Liter |
|---|---|
| L-Alanine, USP/EP | 0.01336 g |
| L-Arginine, HCl, USP | 0.27435 g |
| L-Asparagine H20 | 0.0225 g |
| L-Aspartic acid USP | 0.01995 g |
| Biotin, USP | 0.001 g |
| Calcium chloride, anhydrous | 0.11665 g |
| D-Calcium Pantothenate, USP | 0.00312 g |
| Choline Chloride, USP | 0.00998 g |
| Cupric Sulfate, 5H$_2$0, ACS | 0.000001275 g |
| cyanocobalamin, lisp | 0.00068 g |
| L-Cysteine, HCl, H$_2$O, USP, EP | 0.01756 g |
| L-Cysteine, 2HCl | 0.06256 g |
| Dextrose, Anhydrous, ACS | 1.0 g |
| Ethanolamine, FB | 0.0012 g |
| Ortho Phosphorylethanolamine | 0.0014 g |
| Ferric Nitrate, 9H$_2$0, ACS | 0.00005 g |
| Ferrous Sulfate, 7H$_2$0, ACS | 0.000417 g |
| Folic Acid, USP | 0.00366 g |
| L-Glutamic Acid, EP | 0.02206 g |
| L-Glutamine, USP | 0.73 g |
| L-Glutathione, Reduced | 0.001 g |
| Glycine USP, EP, JP | 0.0262 g |
| L-Histidine, HCl, H$_2$0, EP | 0.07348 g |
| Hypoxanthine 2Na | 0.0027 g |
| i-Inositol | 0.01451 g |
| L-Isoleucine, USP, EP, JP | 0.1057 g |
| L-Leucine, USP, EP, JP | 0.11096 g |
| Linoleic acid | 0.000042 g |
| DL-Alpha-Lipoic Acid | 0.000103 g |
| L-Lysine, HCl, USP, EP, JP | 0.16385 g |
| Magnesium Chloride, 6H$_2$O ACS | 0.061 g |
| Magnesium Sulfate, Anhydrous, USP | 0.04884 g |
| 2-Mercaptoethanol | 0.00039065 g |
| L-Methionine USP, EP, JP | 0.03224 g |
| Phenol Red, Na salt, ACS | 0.0069 g |
| Niacinamide, USP | 0.00302 g |
| L-Phenylalanine, USP, EP | 0.06748 g |
| Potassium Chloride, USP | 0.31182 g |
| L-Proline, USP, EP | 0.02875 g |
| Putrescine, 2HCl | 0.000081 g |
| Pyridoxal HCl | 0.003 g |
| Pyridoxine, HCl, USP | 0.000031 g |
| Riboflavin, USP | 0.000319 g |
| Selenium Dioxide | 0.00000222 g |
| L-Serine, USP, EP | 0.03676 g |
| Sodium Chloride, ACS | 6.1234 g |
| Sodium Phosphate, Dibasic, Anhydrous, USP | 0.07099 g |
| Sodium Phosphate, Monobasic, H$_2$0, USP | 0.0625 g |
| Sodium Pyruvate | 0.055 g |
| Thiamine, HCl, USP | 0.00317 g |
| L-Threonine, USP, EP, JP | 0.10156 g |
| Thymidine | 0.000364 g |
| L-Tryptophan, USP, EP, JP | 0.01902 g |
| L-Tyrosine, 2Na, 2H$_2$0 | 0.10771 g |
| L-Valine, USP, EP, JP | 0.09866 g |
| Zinc Sulfate, 7 H$_2$0, ACS | 0.000432 g |
| D-Mannose | 3.0 g |
| Total | 13.042543120 g/L |

EXAMPLE 3

This example describes an exemplary embodiment of a compounded media powder formulation.

| Component | Units/Liter |
|---|---|
| L-Alanine, USP/EP | 0.01336 g |
| Ammonium Molybdate, 4H$_2$0 | 0.0000037 g |
| L-Arginine, HCl, USP | 0.27435 g |
| L-Asparagine H$_2$0 | 0.045 g |
| L-Aspartic acid USP | 0.01995 g |
| Biotin, USP | 0.001 g |

-continued

| Component | Units/Liter |
|---|---|
| Calcium chloride, anhydrous | 0.11665 g |
| D-Calcium Pantothenate, USP | 0.00312 g |
| Choline Chloride, USP | 0.00998 g |
| Chromic Potassium Sulfate, $12H_2O$ | 0.000001 g |
| Cupric Sulfate, $5H_2O$, ACS | 0.00001375 g |
| cyanocobalamin, USP | 0.00068 g |
| L-Cysteine, HCl, $H_2O$, USP, EP | 0.01756 g |
| L-Cysteine, 2HCl | 0.06256 g |
| Dextrose, Anhydrous, ACS | 1.0 g |
| Ethanolamine, FB | 0.0012 g |
| Ortho Phosphorylethanolamine | 0.0014 g |
| Ferric Nitrate, $9H_2O$, ACS | 0.00005 g |
| Ferrous Sulfate, $7H_2O$, ACS | 0.000417 g |
| Folic Acid, USP | 0.00366 g |
| L-Glutamic Acid, EP | 0.02206 g |
| L-Glutamine, USP | 1.46 g |
| L-Glutathione, Reduced | 0.001 g |
| Glycine. USP, EP, JP | 0.0262 g |
| L-Histidine, FB, USP, EP | 1.552 g |
| L-Histidine, HCl, H20, EP | 0.07348 g |
| Hypoxanthine 2Na | 0.0027 g |
| i-Inositol | 0.01451 g |
| L-Isoleucine, USP, EP, JP | 0.1057 g |
| L-Leucine, USP, EP, JP | 0.11096 g |
| Linoleic acid | 0.000042 g |
| DL-Alpha-Lipoic Acid | 0.000103 g |
| Lithium Chloride | 0.00001 g |
| L-Lysine, HCl, USP, EP, JP | 0.16385 g |
| Magnesium Chloride, Anhydrous | 1.456951840 g |
| Magnesium Sulfate, Anhydrous, USP | 0.04884 g |
| 2-Mercaptoethanol | 0.000390650 g |
| L-Methionine USP, EP, JP | 0.03224 g |
| Niacinamide, USP | 0.00302 g |
| L-Phenylalanine, USP, EP | 0.06748 g |
| Lutrol (R) P-68, NF | 1.0 g |
| Potassium Chloride, USP | 0.31182 g |
| L-Proline, USP, EP | 0.02875 g |
| Putrescine, 2HCl | 0.000081 g |
| Pyridoxal. HCl | 0.003 g |
| Pyridoxine, HCl, USP | 0.000031 g |
| Riboflavin, USP | 0.000319 g |
| Selenium Dioxide | 0.00000222 g |
| L-Serine, USP, EP | 0.07352 g |
| Sodium Chloride, ACS | 6.1234 g |
| Sodium Meta-Silicate, $9H_2O$ | 0.0004263 g |
| Sodium Phosphate, Dibasic, Anhydrous | 0.07099 g |
| Sodium Phosphate, Monobasic, $H_2O$, USP | 0.0625 g |
| Sodium Pyruvate | 0.055 g |
| Thiamine, HCl, USP | 0.00317 g |
| L-Threonine, USP, EP, JP | 0.10156 g |
| Thymidine | 0.000364 g |
| L-Tryptophan, USP, EP, JP | 0.01902 g |
| L-Tyrosine, 2Na, $2H_2O$ | 0.10771 g |
| L-Valine, USP, EP, JP | 0.09866 g |
| Zinc Sulfate, 7 $H_2O$, ACS | 0.000432 g |
| D-Mannose | 3.0 g |
| MOPS, Free Acid, BPC (Sigma M3183) | 1.0465 g |
| MOPS, Sodium, BPC (Sigma M9024) | 3.4680 g |
| Insulin, human recombinant, ACF, USP (#4506) | 0.003 g |
| Ammonium Molybdate $4H_2O$ | 0.0037 mg |
| Chromium Potassium Sulfate $12H_2O$ | 0.001 mg |
| Cupric Sulfate $5H_2O$ | 0.0125 mg |
| Lithium Chloride Anhydrous | 0.01 mg |
| Manganese Sulfate $H_2O$ | 0.000452 mg |
| Sodium Metasilicate $9H_2O$ | 0.4263 mg |
| Total | 22.290808460 g/L |

The compounded cell culture medium powder formulation was hydrated in 1 L of double-deionized sterile $H_2O$ in a hydration tank. The powder was added to the water followed by mixing to ensure adequate dispersion and dissolution. Next, a solution comprising FeSO4 7H2O and ethylenediaminetetraacetic acid (EDTA) was added to the tank. The FeSO4 7H2O and EDTA have the following final concentration in the cell culture medium: about 0.0138 g/L FeSO4 7H2O; and about 0.018625 g/L EDTA. The cell culture media was then stored at 4° C. for later use.

EXAMPLE 4

This example describes an exemplary compounded media powder formulation.

| Component | Units/Liter |
|---|---|
| L-Alanine, USP/EP | 0.01336 g |
| Ammonium Molybdate, $4H_2O$ | 0.0000037 g |
| L-Arginine, HCl, USP | 0.82305 g |
| L-Asparagine $H_2O$ | 0.135 g |
| L-Aspartic acid USP | 0.05985 g |
| Biotin, USP | 0.001 g |
| Calcium chloride, anhydrous | 0.11665 g |
| D-Calcium Pantothenate, USP | 0.00312 g |
| Choline Chloride, USP | 0.00998 g |
| Chromic Potassium Sulfate, $12H_2O$ | 0.000001 g |
| Cupric Sulfate, $5H_2O$, ACS | 0.00001375 g |
| cyanocobalamin, USP | 0.00068 g |
| L-Cysteine, HCl, $H_2O$, USP, EP | 0.01756 g |
| L-Cysteine, 2HCl | 0.06256 g |
| Dextrose, Anhydrous, ACS | 1.0 g |
| Ethanolamine, FB | 0.0012 g |
| Ortho Phosphorylethanolamine | 0.0014 g |
| Ferric Nitrate, $9H_2O$, ACS | 0.00005 g |
| Ferrous Sulfate, $7H_2O$, ACS | 0.000417 g |
| Folic Acid, USP | 0.00366 g |
| L-Glutamic Acid, EP | 0.06618 g |
| L-Glutamine, USP | 1.46 g |
| L-Glutathione, Reduced | 0.001 g |
| Glycine. USP, EP, JP | 0.07878 g |
| L-Histidine, FB, USP, EP | 1.552 g |
| L-Histidine, HCl, H20, EP | 0.07348 g |
| Hypoxanthine 2Na | 0.0027 g |
| i-Inositol | 0.01451 g |
| L-Isoleucine, USP, EP, JP | 0.3171 g |
| L-Leucine, USP, EP, JP | 0.33288 g |
| Linoleic acid | 0.000042 g |
| DL-Alpha-Lipoic Acid | 0.000103 g |
| Lithium Chloride | 0.00001 g |
| L-Lysine, HCl, USP, EP, JP | 0.49155 g |
| Magnesium Chloride, Anhydrous | 1.456951840 g |
| Magnesium Sulfate, Anhydrous, USP | 0.04884 g |
| 2-Mercaptoethanol | 0.000390650 g |
| L-Methionine USP, EP, JP | 0.09672 g |
| Niacinamide, USP | 0.00302 g |
| L-Phenylalanine, USP, EP | 0.20244 g |
| Lutrol (R) P-68, NF | 1.0 g |
| Potassium Chloride, USP | 0.31182 g |
| L-Proline, USP, EP | 0.08625 g |
| Putrescine, 2HCl | 0.000081 g |
| Pyridoxal. HCl | 0.003 g |
| Pyridoxine, HCl, USP | 0.000031 g |
| Riboflavin, USP | 0.000319 g |
| Selenium Dioxide | 0.00000222 g |
| L-Serine, USP, EP | 0.22052 g |
| Sodium Chloride, ACS | 6.1234 g |
| Sodium Meta-Silicate, $9H_2O$ | 0.0004263 g |
| Sodium Phosphate, Dibasic, Anhydrous | 0.07099 g |
| Sodium Phosphate, Monobasic, $H_2O$, USP | 0.0625 g |
| Sodium Pyruvate | 0.055 g |
| Thiamine, HCl, USP | 0.00317 g |
| L-Threonine, USP, EP, JP | 0.30468 g |
| Thymidine | 0.000364 g |
| L-Tryptophan, USP, EP, JP | 0.05706 g |
| L-Tyrosine, 2Na, 2H20 | 0.32313 g |
| L-Valine, USP, EP, JP | 0.29598 g |
| Zinc Sulfate, 7 H20, ACS | 0.000432 g |
| D-Mannose | 3.0 g |
| MOPS, Free Acid, BPC (Sigma M3183) | 1.0465 g |
| MOPS, Sodium, BPC (Sigma M9024) | 3.4680 g |
| Insulin, human recombinant, ACF, USP (#4506) | 0.003 g |
| Ammonium Molybdate $4H_2O$ | 0.0037 mg |

-continued

| Component | Units/Liter |
|---|---|
| Chromium Potassium Sulfate 12H$_2$O | 0.001 mg |
| Cupric Sulfate 5H$_2$O | 0.0125 mg |
| Lithium Chloride Anhydrous | 0.01 mg |
| Manganese Sulfate H$_2$O | 0.000452 mg |
| Sodium Metasilicate 9H$_2$O | 0.4263 mg |
| Total | 24.884908460 g/L |

The compounded cell culture medium powder formulation was hydrated in 1 L of double-deionized sterile H$_2$O in a hydration tank. The powder was added to the water followed by mixing to ensure adequate dissolution. Next, a solution comprising FeSO$_4$ 7H$_2$O and ethylenediaminetetraacetic acid (EDTA) was added to the tank. The FeSO$_4$ 7H$_2$O and EDTA have the following final concentration in the cell culture medium: about 0.0138 g/L FeSO$_4$ 7H$_2$O; and about 0.018625 g/L EDTA. The cell culture media was then stored at 4° C. for later use.

Figure 3:
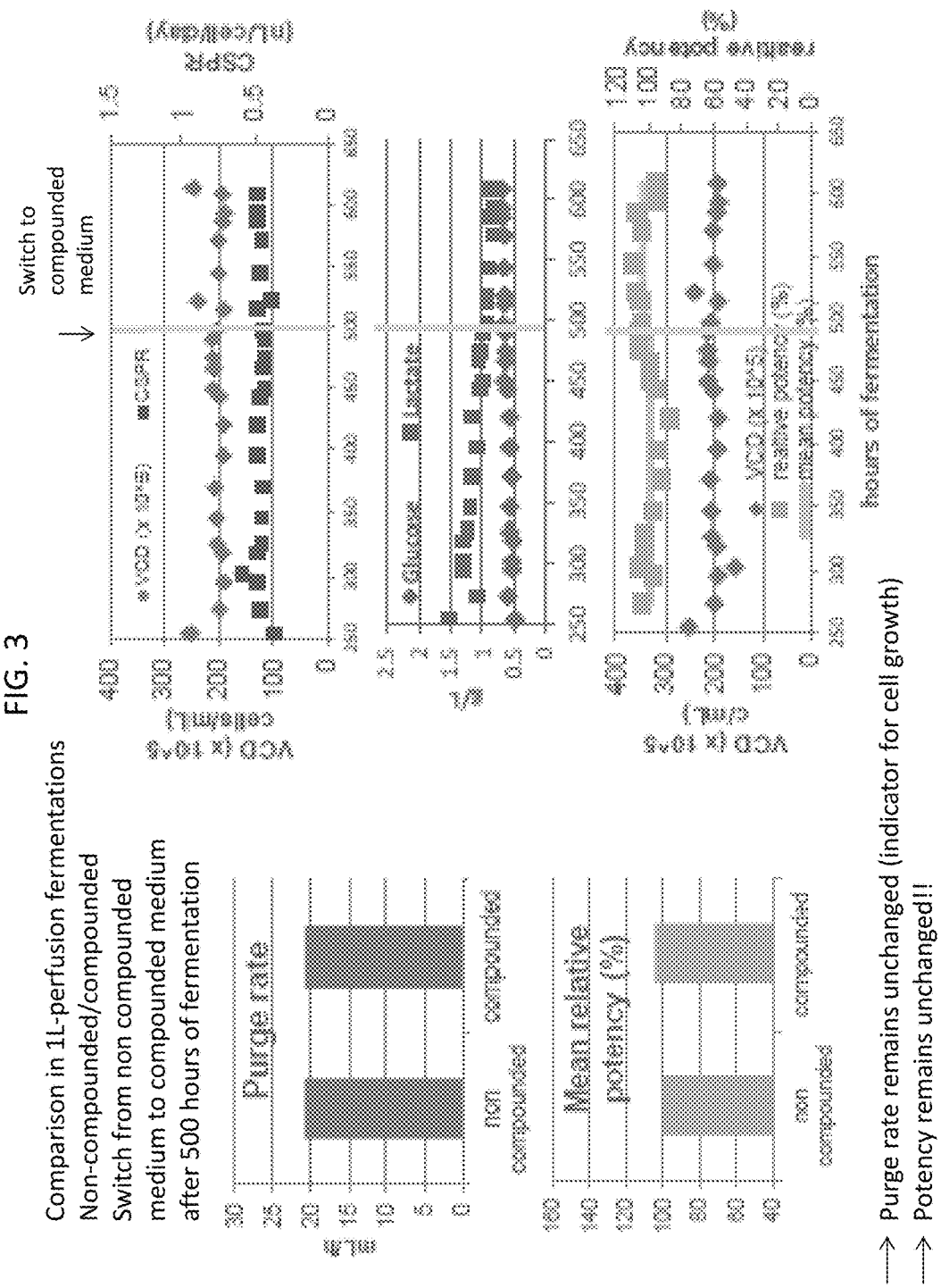
FIG. 3. Cell culture runs using current and compounded method of preparation demonstrated similar growth properties, metabolism and product titer (measured as Potency). Media was prepared the standard way using base media powder (v.1) and sequential supplements addition (FIG. 1) and using compounded media powder (v3.3) with only ferrous sulfate/EDTA addition (FIG. 2) and used to cultivate rFVIII-expressing cells in 1 L perfusion bioreactor runs. No change was apparent in cell culture performance and rFVIII titer (potency) after shifting from non-compounded to compounded medium.

Feasibility of using the (further) compounded medium is demonstrated along two levels: (i) concentration determination following hydration and (ii) cell culture performance studies. Hydration studies show that the concentrations of key media components (in the further compounded medium) are in agreement with the theoretical (expected) values as well as with those in liquid medium prepared the standard way (See Example 1). 1 L perfusion cell culture studies further demonstrate comparable cell culture performance (growth and metabolism) and recombinant protein production (potency/titer) when using either medium preparation method (FIG. 3).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method of making a compounded cell culture medium powder formulation for growing mammalian cells, comprising:

combining a basal medium powder having the following components at the following concentrations upon hydration:
i) 0.0003-0.003 g/L biotin;
ii) 0.035-0.33 g/L calcium chloride;
iii) 0.003-0.03 g/L choline chloride;
iv) 0.0002-0.002 g/L cyanocobalamin (B 12);
v) 1-10 g/L D-mannose;
vi) 0.001-0.01 g/L D-calcium pantothenate;
vii) 0.3-3.0 g/L dextrose (anhydrous);
viii) 0.00003-0.0003 g/L DL-alpha-lipoic acid;
ix) 0.00001-0.00015 g/L ferric nitrate;
x) 0.00005-0.0015 g/L ferrous sulfate;
xi) 0.001-0.01 g/L folic acid;
xii) 0.007-0.20 g/L glycine;
xiii) 0.001-0.01 g/L hypoxanthine 2Na;
xiv) 0.005-0.05 g/LI-inositol;
xv) 0.003-0.03 g/L L-alanine;
xvi) 0.08-1.4 /L L-arginine;
xvii) 0.006-0.16 g/L L-asparagine;
xviii) 0.005-0.10 g/L L-aspartic acid;
xix) 0.005-0.05 g/L L-cysteine HCl;
xx) 0.02-0.2 g/L L-cystine 2HCl;
xxi) 0.005-0.15 g/L L-glutamic acid (anhydrous);

xxii) 0.02-1.5 g/L L-glutamine;
xxiii) 0.0003-0.003 g/L L-glutathione;
xxiv) 0.02-0.2 g/L L-histidine HCl;
xxv) 0.03-0.9 g/L L-isoleucine;
xxvi) 0.03-0.9 g/L L-leucine;
xxvii) 0.05-1.5 g/L L-lysine;
xxviii) 0.01-0.3 g/L L-methionine;
xxix) 0.02-0.6 g/L L-phenylalanine;
xxx) 0.008-0.25 g/L L-proline;
xxxi) 0.009-0.25 g/L L-serine;
xxxii) 0.03-0.9 g/L L-threonine;
xxxiii) 0.006-0.16 g/L L-tryptophan;
xxxiv) 0.02-0.9 g/L L-tyrosine 2Na;
xxxv) 0.03-0.9 g/L L-valine;
xxxvi) 0.01-0.18 g/L magnesium chloride;
xxxvii) 0.02-0.12 g/L magnesium sulfate anhydrous;
xxxviii) 0.001-0.01 g/L niacinamide;
xxxix) 0.0005-0.005 g/L O-phoshphoryl-ethanolamine;
xl) 0.1-1.0 g/L potassium chloride;
xli) 0.00002-0.0002 g/L putrescine 2HCl;
xlii) 0.001-0.01 g/L pyridoxal HCl;
xliii) 0.00001-0.0001 g/L pyridoxine HCl;
xliv) 0.0001-0.001 g/L riboflavin;
xlv) 2.0-15 g/L sodium chloride;
xlvi) 0.01-0.2 g/L sodium phosphate monobasic;
xlvii) 0.02-0.2 g/L sodium phosphate dibasic anhydrous;
xlviii) 0.015-0.15 g/L sodium pyruvate;
xlix) 0.001-0.01 g/L thiamine HCl;
l) 0.0001-0.001 g/L thymidine;
li) 0.00006-0.0015 g/L zinc sulfate;
lii) 0.0000003-0.000006 g/L cupric sulfate;
liii) 0.0000005-0.000008 g/L selenium dioxide;
liv) 0.00001-0.0001 g/L linoleic acid;
lv) 0.0001-0.001 g/L beta-mercaptoethanol;
lvi) 0.0003-0.005 g/L ethanolamine;
with basal media supplement powder having the following components at the following concentrations upon hydration:
a) 0.5-5 g/L magnesium chloride;
b) 0.5-15 mg/mL insulin;
c) one or more additional trace metals selected from the group consisting of:
0.0005-0.01 mg/L ammonium molybdate tetrahydrate,
0.0001-0.01 mg/L chromium potassium sulfate dodecahydrate,
0.001-0.125 mg/L cupric sulfate pentahydrate,
0.001-0.1 mg/L of litium chloride (anhydrous)
0.00004-0.004 mg/L manganese sulfate hydrate, and
0.04-4.2 mg/L of sodium metasilicate nonahydrate;
d) one or more additional amino acid selected from the group consisting of 0.007-0.07 g/L asparagine hydrate, 0.25-2.5 g/L glutamine, 0.5-5 g/L histidine free base, and 0.01-0.1 g/L serine;
e) one or more buffers; and
f) one or more anti-foaming agents,
to make a cell culture medium powder, wherein the cell culture media when hydrated completely dissolves the media components.

* * * * *